United States Patent
Fitzpatrick et al.

(10) Patent No.: US 6,696,290 B2
(45) Date of Patent: Feb. 24, 2004

(54) ERBB2 AND ERBB4 CHIMERIC HETEROMULTIMERIC ADHESINS

(75) Inventors: Vincent Daniel Fitzpatrick, Dayton, NJ (US); Mark Sliwkowski, San Carlos, CA (US); Richard L. Vandlen, Hillsborough, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/267,985

(22) Filed: Mar. 12, 1999

(65) Prior Publication Data

US 2003/0199020 A1 Oct. 23, 2003

Related U.S. Application Data

(63) Continuation of application No. 08/798,326, filed on Feb. 10, 1997, now abandoned.
(60) Provisional application No. 60/021,640, filed on Jul. 12, 1996.

(51) Int. Cl.[7] .................. C07K 16/46; C07K 14/71; C12N 5/10; C12N 15/12
(52) U.S. Cl. .................. 435/325; 436/69.7; 436/320.1; 436/252.3; 436/254.11; 530/350; 530/387.3; 536/23.5; 536/23.4
(58) Field of Search .............. 530/350, 387.3; 435/69.7, 320.1, 325, 252.3, 259.11; 536/23.4, 235

(56) References Cited

U.S. PATENT DOCUMENTS

| | | |
|---|---|---|
| 4,676,980 A | 6/1987 | Segal et al. |
| 4,892,538 A | 1/1990 | Aebischer et al. |
| 5,116,964 A | 5/1992 | Capon et al. |
| 5,225,538 A | 7/1993 | Capon et al. |
| 5,283,187 A | 2/1994 | Aebischer et al. |
| 5,336,603 A | 8/1994 | Capon et al. |
| 5,428,130 A | 6/1995 | Capon et al. |
| 5,447,851 A | 9/1995 | Beutler et al. |
| 5,455,165 A | 10/1995 | Capon et al. |
| 5,514,582 A | 5/1996 | Capon et al. |
| 5,565,335 A | 10/1996 | Capon et al. |

(List continued on next page.)

FOREIGN PATENT DOCUMENTS

| | | |
|---|---|---|
| WO | WO 89/02922 | 4/1989 |
| WO | WO 91/00360 | 1/1991 |
| WO | WO 94/00140 | 1/1994 |
| WO | WO 94/04690 | 3/1994 |
| WO | WO 95/14930 | 6/1995 |
| WO | WO 95/25795 | 9/1995 |
| WO | WO 95/27061 | 10/1995 |

OTHER PUBLICATIONS

Tzahar, et al., Mol. Cell Biol. 16(10):5276–87, Dec. 1996.*
Pinkas–Kramarski et al., The EMBO Journal 15(10):2452–67, 1996.*
Chamow et al., Trends in Biotechnology 14:52–60, Feb. 1996.*

(List continued on next page.)

Primary Examiner—Lorraine Spector
Assistant Examiner—Claire M. Kaufman
(74) Attorney, Agent, or Firm—Merchant & Gould P.C.

(57) ABSTRACT

Novel chimeric heteromultimer adhesins that bind the ligand of natural heteromultimeric receptors and uses therefor are disclosed. The chimeric molecules of the heteromultimer adhesins comprise an extracellular domain of a heteromultimeric receptor monomer and a multimerization domain for the stable interaction of the chimeric molecules in the adhesin. Specifically disclosed are heteromultimeric adhesins comprising the extracellular domains of ErbB2 and ErbB3 or ErbB2 and ErbB4. The chimeric ErbB heteromultimer adhesins of the present invention are useful as competitive antagonists or agonists of a neuregulin for the treatment of diseases such as various cancers.

9 Claims, 6 Drawing Sheets

U.S. PATENT DOCUMENTS

| | | | |
|---|---|---|---|
| 5,714,147 A | | 2/1998 | Capon et al. |
| 5,726,037 A | | 3/1998 | Bodary et al. |
| 5,726,290 A | | 3/1998 | Bodary et al. |
| 5,731,168 A | | 3/1998 | Carter et al. |
| 5,804,396 A | * | 9/1998 | Plowman .................. 435/7.23 |
| 5,807,706 A | * | 9/1998 | Carter et al. ............... 435/69.1 |
| 5,821,333 A | | 10/1998 | Carter et al. |
| 6,117,655 A | | 9/2000 | Capon et al. |

OTHER PUBLICATIONS

Ashkenazi et al., "Protection Against Endotoxic Shock by a Tumor Necrosis Factor Receptor Immunoadhesin" *Proc. Natl. Acad. Sci.* 88:10535–10539 (1991).

Banner et al., "Crystal Structure of the Soluble Human 55 kd TNF Receptor–Human TNFβ Complex: Implications for TNF Receptor Activation" *Cell* 73:431–445 (1993).

Beerli et al., "Neu Differentiation Factor Activation of ErbB–3 and ErbB–4 is Cell Specific and Displays a Differential Requirement for ErbB–2" *Molecular & Cellular Biology* 15:6496–6505 (Dec. 1995).

Brennan et al., "Preparation of bispecific antibodies by chemical recombination of monoclonal immunoglobulin $G_1$ fragments" *Science* 229:81–83 (Jul. 1985).

Brown et al., "The Extracellular Domain of the Epidermal Growth Factor Receptor" *European Journal of Biochemistry* 225:223–233 (1994).

Carpenter, "Receptors for Epidermal Growth Factor and Other Polypeptide Mitogens" *Ann. Rev. Biochem.* 56:881–914 (1987).

Chamow et al., "Immunoadhesins: Principles and Applications" *Trends in Biotechnology* 14:52–60 (1996).

Chang et al., "Modulation of Growth Factor Receptor Function by Isoform Heterodimerization" *Proc. Natl. Acad. Sci. USA* 93:5947–5952 (1996).

Collesi et al., "A Splicing Variant of the RON Transcript Induces Constitutuive Tyrosine Kinase Activity and an Invasive Phenotype" *Molecular & Cellular Biology* 16(10):5518–5526 (1996).

Dietrich et al., "Role of CD3γ in T Cell Receptor Assembly" *Journal of Cell Biology* 132(3):299–310 (1996).

Dietsch et al., "Bispecific Receptor Globulins, Novel Tools for the Study of Cellular Interactions" *Journal of Immunological Methods* 162:123–132 (1993).

Ellison et al., "The nucleotide sequence of a human immunoglobulin $C_{\gamma 1}$ gene" *Nucleic Acids Research* 10(13):4071–4079 (1982).

Fendly et al., "Characterization of Murine Monoclonal Antibodies Reactive to Either the Human Epidermal Growth Factor Receptor or HER2/neu Gene Product" *Cancer Research* 50:1550–1558 (Mar. 1, 1990).

Ganong *Review of Medical Physiology*, 17th edition, Norwalk, Connecticut:Appleton & Lange pp. 580 (1995).

Gascoigne et al., "Secretion of a Chimeric T–cell Receptor–immunoglobulin Protein" *Proc. Natl. Acad. Sci. USA* 84:2936–2940 (1987).

Gorman et al., "Transient Production of Proteins Using an Adenovirus Transformed Cell Line" *DNA Prot. Eng. Tech.* 2(1):3–10 (1990).

Gruber et al., "Efficient Tumor Cell Lysis Mediated by a Bispecific Single Chain Antibody Expressed in *Escherichia Coli*" *Journal of Immunology* 152:5368–5374 (1994).

Holliger et al., ""Diabodies": Small bivalent and bispecific antibody fragments" *Proc. Natl. Acad. Sci. USA* 90:6444–6448 (Jul. 1993).

Horan et al., "Binding of Neu Differentiation Factor with the Extracellular Domain of Her2 and Her3" *Journal of Biological Chemistry* 270(41):24604–24608 (1995).

Kainu et al., "The Dioxin Receptor and its Nuclear Translocator (Arnt) in the Rat Brain" *Neuroreport* 6:2557–2560 (1995).

Karunagaran et al., "ErbB–2 is a Common Auxiliary Subunit of NDF and EGF Receptors: Implications for Breast Cancer" *EMBO Journal* 15(2):254–264 (1996).

Kendall et al., "Identification of a Natural Soluble Form of the Vascular Endothelial Growth Factor Receptor, FLT–1, and Its Heterodimerization with KDR" *Biochem. & Biophys. Res. Comm.* 226:324–328 (1996).

King et al., "Ligand–Independent tyrosine phosphorylation of EGF receptor and the erbB–2/neu proto–oncogene product is induced by hyperosmotic shock" *Oncogene* 4(1):13–18 (Jan. 1989).

Kishimoto et al., "Cytokine Signal Transduction" *Cell* 76:253–262 (Jan. 28, 1994).

Kokai et al., "Synergistic Interaction of p185c–neu and the EGF Receptor Leads to Transformation of Rodent Fibroblasts" *Cell* 58:287–292 (1989).

Kostelny et al., "Formation of a Bispecific Antibody by the Use of Leucine Zippers" *Journal of Immunology* 148(5):1547–1553 (1992).

Lala et al., "Activation of Specific RXR Heterodimers by an Antagonist of RXR Homodimers" *Nature* 383:450–453 (1996).

Lemke, "Neuregulins in Development" *Molecular and Cellular Neuroscience* 7:247–262 (1996).

Levi et al., "The functional characteristics of Schwann Cells cultured from human peripheral nerve after transplantation into a gap within the rat sciatic nerve" *J. Neuroscience* 14(3):1309–1319 (1994).

Levi et al., "The influence of Heregulins on Human Schwann Cell Proliferation" *J. Neuroscience* 15(2):1329–1340 (Feb. 1995).

Lewis et al., "Growth regulation of human breast and ovarian tumor cells by heregulin: Evidence for the requirement of ErbB2 as a critical component in mediating heregulin responsiveness" *Cancer Research* 56:1457–1465 (1996).

Li et al., "Identification of Gas6 as a Growth Factor for Human Schwann Cells" *The Journal of Neuroscience* 16(6):2012–2019 (Mar. 15, 1996).

Marsters et al., "Interferon γ Signals Via a High–Affinity Multisubunit Receptor Complex That Contains Two Types of Polypeptide Chain" *Proc. Natl. Acad. Sci. USA* 92:5401–5405 (1995).

McBain et al., "N–Methyl–D–Aspartic Acid Receptor Structure and Function" *Physiological Reviews* 74(3):723–760 (Jul. 1994).

Meyer & Birchmeier, "Distinct isoforms of neuregulin are expressed in mesenchymal and neuronal cells during mouse development" *Proc. Natl. Acad. Sci.* 91:1064–1068 (1994).

Morrissey et al., "Axon–induced mitogenesis of human Schwann cells involves heregulin and p185$^{erbB2}$" *Proc. Natl. Acad. Sci. USA* 92:1431–1435 (Feb. 1995).

Murali et al., "Structural Analysis of p185$^{c-neu}$ and Epidermal Growth Factor Receptor Tyrosine Kinases: Oligomerization of Kinase Domains" *Proc. Natl. Acad. Sci. USA* 93:6252–6257 (1996).

Nagaya et al., "Heterodimerization Preferences of Thyroid Hormone Receptor α Isoforms" *Biolchem. Biophys. Res. Comm.* 226:426–430 (1996).

Pennica et al., "Cardiotrophin–1. Biological Activities and Binding to the Leukemia Inhibitory Factor Receptor/gp130 Signaling Complex" *Journal of Biological Chemistry* 270(1):10915–10922 (1995).

Perez et al., "Identification of Two Isoforms of the Cak Receptor Kinase that are Co–expressed in Breast Tumor Cell Lines" *Oncogene* 12:1469–1477 (1996).

Pinkas–Kramarski et al., "Brain neurons and glial cells express Neu differentiation factor/heregulin: A survival factor for astrocytes" *Proc. Natl. Acad. Sci. USA* 91:9387–9391 (1994).

Pinkas–Kramarski et al., "Diversification of Neu Differentiation Factor and Epidermal Growth Factor Signaling by Combinatorial Receptor Interactions" *EMBO Journal* 15(10):2452–2467 (1996).

Plowman et al., "Heregulin induces tyrosine phosphorylation of HER4/p180$^{erbB4}$" *Nature* (Letters to Nature) 366:473–475 (Dec. 2, 1993).

Plowman et al., "Ligand–specific activation of HER4/p180$^{erbB4}$, a fourth member of the epidermal growth factor receptor family" *Proc. Natl. Acad. Sci. USA* 90:1746–1750 (1993).

Shalaby et al., "Development of Humanized Bispecific Antibodies Reactive with Cytotoxic Lymphocytes and Tumor Cells Overexpressing the HER2 Protooncogene" *Journal of Experimental Medicine* 175:217–225 (Jan. 1, 1992).

Shtrom et al., "Formation of a Ligand–binding Site for the Acetylcholine Receptor in Vitro" *Journal of Biological Chemistry* 271(41):25506–25514 (1996).

Sliwkowski et al., "Coexpression of erbB2 and erbB3 proteins reconstitutes a high affinity receptor for heregulin" *Journal of Biological Chemistry* 269(20):14661–14665 (1994).

Stern et al., "EGF–stimulated Tyrosine Phosphorylation of p185$^{neu}$: a potential model for receptor interactions" *EMBO Journal* 7(4):995–1001 (1988).

Taga, "gp130, a Shared Signal Transducing Receptor Component for Hematopoietic and Neuropoietic Cytokines" *J. Neurochem.* 67(1):1–10 (1996).

Tanahashi et al., "Identification of a 79–kDa Heparin–binding Fibroblast Growth Factor (FGF) Receptor in Rat Hepatocytes and Its Correlation with the Different Growth Responses to FGF–1 between Hepatocyte Subpopulations" *Journal of Biological Chemistry* 271(14):8221–8227 (1996).

Tutt et al., "Trispecific F(ab')$_3$ Derivatives that Use Cooperative Signaling Via the TCR/CD3 Complex and CD2 to Activate and Redirect Resting Cytotoxic T Cells" *J. Immunol.* 147(1):60–69 (1991).

Tzahar et al., "A Hierarchical Network of Interreceptor Interactions Determines Signal Transduction by Neu Differentiation Factor/Neuregulin and Epidermal Growth Factor" *Molecular & Cellular Biology* 16(10):5276–5287 (1996).

Tzahar et al., "ErbB–3 and ErbB–4 Function as the Respective Low and High Affinity Receptors of All Neu Differentiation Factor/Heregulin Isoforms" *Journal of Biological Chemistry* 269(40):25226–25233 (1994).

Ullrich and Schlessinger, "Signal Transduction by Receptors with Tyrosine Kinase Activity" *Cell* 61:203–212 (Apr. 1990).

Wada et al., "Intermolecular Association of the p185$^{neu}$ Protein and EGF Receptor Modulates EGF Receptor Function" *Cell* 61:1339–1347 (1990).

Wells, "Binding in the Growth Hormone Receptor Complex" *Proc. Natl. Acad. Sci. USA* 93:1–6 (1996).

Wells, J., "Structural and functional basis for hormone binding and receptor oligomerization" *Cell Biology* 6:163–173 (1994).

Wollert et al., "Cardiotrophin–1 Activates a Distinct Form of Cardiac Muscle Cell Hypertrophy" *Journal of Biological Chemistry* 271(16):9535–9545 (1996).

Yoo et al., "Effects of pH and $Ca^{2+}$ on Heterodimer Formation by Chromogranin A and Chromogranin B" *Journal of Biological Chemistry* 271(29):17041–17046 (1996).

Zhou et al., "Real–Time Measurements of Kinetics of EGF Binding to Soluble EGF Receptor Monomers and Dimers Support the Dimerization Model for Receptor Activation" *Biochemistry* 32:8193–8198 (1993).

Ziegler et al., "Molecular Cloning and Characterization of a Novel Receptor Protein Tyrosine Kinase from Human Placenta" *Oncogene* 8:663–670 (1993).

* cited by examiner

Models For the Interaction of ErbB2 With ErbB3 or ErbB4

CONTACT    CONFORMATIONAL

ERBB2 AND ERBB4 CHIMERIC HETEROMULTIMERIC ADHESINS

CROSS REFERENCE TO RELATED APPLICATIONS

This is a continuation application of U.S. Ser. No. 08/798,326 filed on Feb 10, 1997, now abandoned, which is a non-provisional application filed under 37 CFR 1.53(b)(1), claiming priority under U.S.C. Section 119(e) to provisional Application Serial No. 60/021,640, filed Jul. 12, 1996, now abandoned.

FIELD OF THE INVENTION

This application relates generally to chimeric heteromultimer adhesins comprising extracellular binding domains of heteromultimeric receptors, which heteromultimer adhesins bind the ligand of the natural receptor. The invention further relates to antibodies to the heteroadhesins, methods of making the adhesins and methods of using the heteroadhesins and antibodies.

BACKGROUND OF THE INVENTION

Transduction of signals that regulate cell growth and differentiation is regulated in part by phosphorylation of various cellular proteins. Protein tyrosine kinases are enzymes that catalyze this process. Receptor protein tyrosine kinases are believed to direct cellular growth via ligand-stimulated tyrosine phosphorylation of intracellular substrates.

The ErbB family of single-spanning, receptor tyrosine kinases consists of four members: epidermal growth factor receptor (EGFR), ErbB2 (HER2/neu), ErbB3 (HER3) and ErbB4 (HER4). A number of ligands, all of which are different gene products, have been identified that bind and activate EGFR (reviewed in Groenen et al., 1994). In contrast, a single neuregulin gene encodes for a large number of protein isoforms that result from alternative splicing of mRNA transcripts (reviewed in (Lemke, G. (1996) mol. Cell. Neurosci. 7:247–262). ErbB3 (Carraway, K. L. et al. (1994) J. Biol. Chem. 269:14303–14306) or ErbB4 (Plowman, G. D. et al., (1993) Nature 366:473–475) can serve as receptors for the neuregulins. These receptors and ligands play key roles in normal cell growth and differentiation.

Growth factor receptor protein tyrosine kinases of the class I subfamily include the 170 kDa epidermal growth factor receptor (EGFR) encoded by the erbB1 gene. erbB1 has been causally implicated in human malignancy. In particular, increased expression of this gene has been observed in more aggressive carcinomas of the breast, bladder, lung and stomach (Modjtahedi, H. and Dean, C. (1994) Int. J. Oncol. 4:277–296).

The second member of the class I subfamily, p185$^{neu}$, was originally identified as the product of the transforming gene from neuroblastomas of chemically treated rats. The neu gene (also called erbB2 and HER2) encodes a 185 kDa receptor protein tyrosine kinase. Amplification and/or overexpression of the human HER2 gene correlates with a poor prognosis in breast and ovarian cancers (Slamon, D. J. et al., Science 235:177–182 (1987); and Slamon et al., Science 244:707–712 (1989)). Overexpression of HER2 has been correlated with other carcinomas including carcinomas of the stomach, endometrium, salivary gland, lung, kidney, colon and bladder. Accordingly, Slamon et al. in U.S. Pat. No. 4,968,603 describe and claim various diagnostic assays for determining HER2 gene amplification or expression in tumor cells. Slamon et al. discovered that the presence of multiple gene copies of HER2 oncogene in tumor cells indicates that the disease is more likely to spread beyond the primary tumor site, and that the disease may therefore require more aggressive treatment than might otherwise be indicated by other diagnostic factors. Slamon et al. conclude that the HER2 gene amplification test, together with the determination of lymph node status, provides greatly improved prognostic utility.

A further related gene, called erbB3 or HER3, has also been described. See U.S. Pat. No. 5,183,884; Kraus et al., Proc. Natl. Acad. Sci. USA 86:9193–9197 (1989); EP Pat Appln No 444,961A1; and Kraus et al., Proc. Natl. Acad. Sci. USA 90:2900–2904 (1993). Kraus et al. (1989) discovered that markedly elevated levels of erbB3 mRNA were present in certain human mammary tumor cell lines indicating that erbB3, like erbB1 and erbB2, may play a role in human malignancies. Also, Kraus et al. (1993) showed that EGF-dependent activation of the ErbB3 catalytic domain of a chimeric EGFR/ErbB3 receptor resulted in a proliferative response in transfected NIH-3T3 cells. Furthermore, these researchers demonstrated that some human mammary tumor cell lines display a significant elevation of steady-state ErbB3 tyrosine phosphorylation further indicating that this receptor may play a role in human malignancies. The role of erbB3 in cancer has been explored by others. It has been found to be overexpressed in breast (Lemoine et al., Br. J. Cancer 66:1116–1121 (1992)), gastrointestinal (Poller et al., J. Pathol. 168:275–280 (1992), Rajkumer et al., J. Pathol. 170:271–278 (1993), and Sanidas et al., Int. J. Cancer 54:935–940 (1993)), and pancreatic cancers (Lemoine et al., J. Pathol. 168:269–273 (1992), and Friess et al., Clinical Cancer Research 1:1413–1420 (1995)).

ErbB3 is unique among the ErbB receptor family in that it possesses little or no intrinsic tyrosine kinase activity (Guy et al., Proc. Natl. Acad. Sci. USA 91:8132–8136 (1994) and Kim et al. J. Biol. Chem. 269:24747–55 (1994)). When ErbB3 is co-expressed with ErbB2, an active signaling complex is formed and antibodies directed against ErbB2 are capable of disrupting this complex (Sliwkowski et al., J. Biol. Chem., 269(20):14661–14665 (1994)). Additionally, the affinity of ErbB3 for heregulin (HRG) is increased to a higher affinity state when co-expressed with ErbB2. See also, Levi et al., Journal of Neuroscience 15: 1329–1340 (1995); Morrissey et al., Proc. Natl. Acad. Sci. USA 92: 1431–1435 (1995); Lewis, G. D. et al., Cancer Res., 56:1457–1465 (1996); Pinkas-Kramarski, R. et al. (1996) EMBO J. 15:2452–2467; Beerli, R. et al. (1995) Mol. Cell. Biol. 15:6496–6505; and Karunagaran, D. et al. (1996) EMBO J. 15:254–264 with respect to the in vivo ErbB2–ErbB3 protein complex.

The class I subfamily of growth factor receptor protein tyrosine kinases has been further extended to include the HER4/Erb4 receptor. See EP Pat Appln No 599,274; Plowman et al., Proc. Natl. Acad. Sci. USA 90:1746–1750 (1993); and Plowman et al., Nature 366:473–475 (1993). Plowman et al. found that increased HER4 expression closely correlated with certain carcinomas of epithelial origin, including breast adenocarcinomas. Diagnostic methods for detection of human neoplastic conditions (especially breast cancers) which evaluate HER4 expression are described in EP Pat Appln No. 599,274.

The quest for the activator of the HER2 oncogene has lead to the discovery of a family of heregulin polypeptides. These proteins appear to result from alternate splicing of a single gene which was mapped to the short arm of human chromosome 8 by Lee, J. and Wood, W. I. (1993) Genomics 16:790–791).

Holmes et al. isolated and cloned a family of polypeptide activators for the HER2 receptor which they called heregulin-α (HRG-α), heregulin-β1 (HRG-β1), heregulin-β2 (HRG-β2), heregulin-β2-like (HRG-β2-like), and heregulin-β3 (HRG-β3). See Holmes, W. E. et al., Science 256:1205–1210 (1992); WO 92/20798; and U.S. Pat. No. 5,367,060. The 45 kDa polypeptide, HRG-α, was purified from the conditioned medium of the MDA-MB-231 human breast cancer cell line. These researchers demonstrated the ability of the purified heregulin polypeptides to activate tyrosine phosphorylation of the HER2 receptor in MCF7 breast tumor cells. Furthermore, the mitogenic activity of the heregulin polypeptides on SK-BR-3 cells (which express high levels of the HER2 receptor) was illustrated. Like other growth factors which belong to the EGF family, soluble HRG polypeptides appear to be derived from a membrane bound precursor (called pro-HRG) which is proteolytically processed to release the 45 kDa soluble form. These pro-HRGs lack a N-terminal signal peptide.

While heregulins are substantially identical in the first 213 amino acid residues, they are classified into two major types, α and β, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-α, and 27% identical to EGF.

The 44 kDa neu differentiation factor (NDF), which is the rat equivalent of human HRG, was first described by Peles et al., Cell, 69:205–216 (1992); and Wen et al., Cell, 69:559–572 (1992). Like the HRG polypeptides, NDF has an immunoglobulin (Ig) homology domain followed by an EGF-like domain and lacks a N-terminal signal peptide. Subsequently, Wen et al., Mol. Cell. Biol., 14(3):1909–1919 (1994) carried out "exhaustive cloning" to extend the family of NDFs. This work revealed six distinct fibroblastic pro-NDFs. Adopting the nomenclature of Holmes et al., the NDFs are classified as either α or β polypeptides based on the sequences of the EGF-like domains. Isoforms 1 to 4 are characterized on the basis of the variable membrane stretch (between the EGF-like domain and transmembrane domain). Also, isoforms a, b and c are described which have variable length cytoplasmic domains. These researchers conclude that different NDF isoforms are generated by alternative splicing and perform distinct tissue-specific functions. See also EP 505 148; WO 93/22424; and WO 94/28133 concerning NDF.

While the heregulin polypeptides were first identified based on their ability to activate the HER2 receptor (see Holmes et al., supra), it was discovered that certain ovarian cells expressing neu and neu-transfected fibroblasts did not bind or crosslink to NDF, nor did they respond to NDF to undergo tyrosine phosphorylation (Peles et al., EMBO J. 12:961–971 (1993)). This indicated another cellular component was necessary for conferring full heregulin responsiveness. Carraway et al. subsequently demonstrated that $^{125}$I-rHRGβ1$_{177-244}$ bound to NIH-3T3 fibroblasts stably transfected with bovine erbB3 but not to non-transfected parental cells. Accordingly, they conclude that ErbB3 is a receptor for HRG and mediates phosphorylation of intrinsic tyrosine residues as well as phosphorylation of ErbB2 receptor in cells which express both receptors. Carraway et al., J. Biol. Chem. 269(19):14303–14306 (1994). Sliwkowski et al., J. Biol. Chem. 269(20):14661–14665 (1994) found that cells transfected with HER3 alone show low affinities for heregulin, whereas cells transfected with both HER2 and HER3 show higher affinities.

This observation correlates with the "receptor cross-talking" described previously by Kokai et al., Cell 58:287–292 (1989); Stern et al., EMBO J. 7:995–1001 (1988); and King et al., 4:13–18 (1989). These researchers found that binding of EGF to the EGFR resulted in activation of the EGFR kinase domain and cross-phosphorylation of p185$^{HER2}$. This is believed to be a result of ligand-induced receptor heterodimerization and the concomitant cross-phosphorylation of the receptors within the heterodimer (Wada et al., Cell 61:1339–1347 (1990)).

Plowman and his colleagues have similarly studied p180$^{HER4}$/p185$^{HER2}$ activation. They expressed p185$^{HER2}$ alone, p180$^{HER4}$ alone, or the two receptors together in human T lymphocytes and demonstrated that heregulin is capable of stimulating tyrosine phosphorylation of p180$^{HER4}$, but could only stimulate p185$^{HER2}$ phosphorylation in cells expressing both receptors. Plowman et al., Nature 336:473–475 (1993). Thus, heregulin is an example of a member of the EGF growth factor family that can interact with several receptors (Carraway and Cantley, Cell 78:5–8 (1994)). Additionally, the β-cellulin ligand has been shown to bind to the EGF receptor and HER4, but does not bind HER3 (Riese II, D. J. et al. (1996) Oncogene 12:345–353).

The biological role of heregulin has been investigated by several groups. For example, Falls et al., (Cell 72:801–815 (1993)) found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in chick muscle. Corfas and Fischbach, J. Neuroscience, 13(5): 2118–2125 (1993). It has also been shown that GGFII is mitogenic for subconfluent quiescent human myoblasts and that differentiation of clonal human myoblasts in the continuous presence of GGFII results in greater numbers of myotubes after six days of differentiation (Sklar et al., J. Cell Biochem., Abst. W462, 18D, 540 (1994)). See also WO 94/26298 published Nov. 24, 1994.

Holmes et al., supra, found that HRG exerted a mitogenic effect on mammary cell lines (such as SK-BR-3 and MCF-7). The mitogenic activity of GGFs on Schwann cells has also been reported. See, e.g., Brockes et al., J. Biol. Chem. 255(18):8374–8377 (1980); Lemke and Brockes, J. Neurosci. 4:75–83 (1984); Brockes et al., J. Neuroscience 4(1):75–83 (1984); Brockes et al., Ann. Neurol. 20(3):317–322 (1986); Brockes, J., Methods in Enzym., 147: 217–225 (1987) and Marchionni et al., supra. Schwann cells provide myelin sheathing around the axons of neurons, thereby forming individual nerve fibers. Thus, it is apparent that Schwann cells play an important role in the development, function and regeneration of peripheral nerves. The implications of this from a therapeutic standpoint have been addressed by Levi et al., J. Neuroscience 14(3):1309–1319 (1994). Levi et al. discuss the potential for construction of a cellular prosthesis comprising human Schwann cells which could be transplanted into areas of damaged spinal cord. Methods for culturing Schwann cells ex vivo have been described. See WO 94/00140 and Li et al., J. Neuroscience 16(6):2012–2019 (1996).

Pinkas-Kramarski et al. found that NDF seems to be expressed in neurons and glial cells in embryonic and adult rat brain and primary cultures of rat brain cells, and suggested that it may act as a survival and maturation factor for astrocytes (Pinkas-Kramarski et al., PNAS, USA 91:9387–9391 (1994)). Meyer and Birchmeier, PNAS, USA 91:1064–1068 (1994) analyzed expression of heregulin during mouse embryogenesis and in the perinatal animal using in situ hybridization and RNase protection experiments. These authors conclude that, based on expression of this molecule, heregulin plays a role in vivo as a mesenchymal and neuronal factor. Also, their findings imply that heregulin functions in the development of epithelia. Similarly, Danilenko et al., Abstract 3101, FASEB 8(4–5):A535 (1994), found that the interaction of NDF and the HER2 receptor is important in directing epidermal migration and differentiation during wound repair.

Interaction of ErbB family members has been investigated in vitro and in vivo. Transactivation of ErbB2 as a result of ligand interaction with other ErbB family members is a common and physiologically important occurrence (Dougall, W. C. et al., (1993) J. Cell. Biochem. 53:61–73; Earp, H. S. et al., (1995) Breast Cancer Res. Treatment 35:115–132). Co-expression of ErbB2 with ErbB3 leads to the formation of a high affinity heregulin (HRG) binding site (Sliwkowski, M. X. et al., (1994) J. Biol. Chem. 269:14661–14665). ErbB2 modulates the affinity of ErbB3 for HRG and appears to provide tyrosine kinase activity to the ErbB3-HRG complex, since ErbB3 is a dysfunctional signaling receptor lacking intrinsic tyrosine kinase activity (Guy, P. M. et al., (1994) PNAS USA 91:8132–8136). Physio-chemical studies have not shown association of the ECDs of ErbB2 and ErbB3 in vitro (Horan et al., J. Biol. Chem. 270:24604–24608 (1995)). In addition, binding of neu differentiation factor (NDF) to soluble HER3 was not enhanced by the presence of soluble HER2.

SUMMARY OF THE INVENTION

The invention relates to the surprising discovery that soluble chimeric heteromultimers comprising the extracellular domains of heteromultimeric receptor monomers bind the receptor ligand. The invention further relates to methods of making the chimeric heteromultimers, methods of using them as receptor ligand antagonists, antibodies to the chimeric heteromultimers that function as antagonists or agonists of the receptor ligand, and methods of treating a disease state related to ligand-receptor interaction.

In one aspect the invention includes a chimeric heteromultimer comprising a first amino acid sequence, which sequence forms a chimeric monomer and comprises an extracellular domain (ECD) or ligand binding fragment thereof, of a first monomer of a natural heteromultimeric receptor and a multimerization domain, wherein the ECD is fused to the multimerization domain. The chimeric heteroadhesin of the invention further comprises an additional amine acid sequence forming an additional chimeric monomer comprising an extracellular domain of an additional monomer of the natural heteromultimeric receptor and a multimerization domain. According to this aspect of the invention the extracellular domains of the first and additional monomers of the natural heteromultimeric receptor are associated in a cell to form a natural heteromultimeric receptor which is activated upon binding of a ligand, and wherein the soluble chimeric heteromultimer adhesin has $10^{-1}$ to $10^6$ fold affinity for the ligand relative to a monomer of the natural receptor or a homomultimer of the natural receptor. In a preferred embodiment of the invention the chimeric heteromultimer adhesin is an aqueous soluble adhesin.

In an embodiment of the invention, the chimeric heteromultimer adhesin is an antagonist of the ligand that binds to the extracellular domains of the natural heteromultimeric receptor.

In another embodiment of the invention, the multimerization domain of the first amino acid sequence is capable of interacting with the multimerization domain of each additional amino acid sequence to form a heteromultimer.

In yet another embodiment of the invention the chimeric heteromultimer adhesin comprises a multimerization domain which includes an immunoglobulin region, preferably an immunoglobulin constant region, such as from IgG1, IgG2, IgG3, IgG4, IgM, and IgF.

In still another embodiment of the invention, the chimeric heteroadhesin includes a multimerization domain capable of forming a stable protein-protein interaction. Such protein-protein interaction domains (or multimerization domains) include a leucine zipper, an amino acid sequence comprising a protuberance complementary to an amino acid sequence comprising a hole, a hydrophobic domain, a hydrophilic domain, and an amino acid sequence comprising a free thiol moiety capable of reacting to form an intermolecular disulfide bond with a multimerization domain of an additional amino acid sequence.

A further embodiment of the invention is a chimeric heteromultimer adhesin in which the first amino acid sequence comprising an extracellular domain of the ErbB2 receptor monomer, an additional amino acid sequence comprising an extracellular domain of the ErbB3 receptor monomer, and a multimerization domain of the first and additional amino acids each comprises an immunoglobulin constant region. The multimerization domain provides for the formation of a stable protein-protein interaction between the first and additional amino acid sequences. A preferred ligand of this chimeric heteroadhesin is the ligand, heregulin.

A further embodiment of the invention is a chimeric heteromultimer adhesin in which the first amino acid sequence comprising an extracellular domain of the ErbB2 receptor monomer, an additional amino acid sequence comprising an extracellular domain of the ErbB4 receptor monomer, and a multimerization domain of the first and additional amino acids each comprises an immunoglobulin constant region. The multimerization domain provides for the formation of a stable protein-protein interaction between the first and additional amino acid sequences. A preferred ligand of this chimeric heteroadhesin is the ligand, heregulin.

In another aspect, the invention includes an isolated nucleic acid sequence encoding an amino acid sequence of the chimeric heteromultimer adhesin of the invention.

In other embodiments, the invention provides an isolated nucleic acid molecule encoding the chimeric amino acid sequence of a monomer of the heteromultimer adhesin such as, for example, ErbB2-IgG, ErbB3-IgG, or ErbB4-IgG. For example, the nucleic acid molecule may be selected from the group consisting of: (a) a nucleic acid comprising the nucleotide sequence of the extracellular domain (i.e. a ligand binding domain or binding fragment thereof) of a monomer of a natural heteromultimeric receptor covalently attached in phase and in the direction of transcription to a nucleic acid sequence encoding a multimerization domain, such as an immunoglobulin constant domain; and (b) a nucleic acid corresponding to the sequence of (a) within the scope of degeneracy of the genetic code. The isolated nucleic acid molecule optionally further comprises a promoter operably linked thereto.

The isolated nucleic acid may also be used for in vivo or ex vivo gene therapy. This embodiment of the invention encompasses the administration of the nucleic acid of the invention, a vector comprising the nucleic acid, or a cell comprising the nucleic acid to a mammal such that the encoded chimeric adhesin is expressed in the mammal and acts as an antagonist of its ligand. For example, ErbB2/3-IgG expressed in a mammal is useful to reduce the local concentration of heregulin near a ErbB2/3 receptor and inhibit growth of a cell having the receptor on its surface. Preferably the expressed ErbB2/3-IgG is used to treat a cell proliferative disease, such as a cancer, in which antagonizing heregulin binding to its receptor inhibits cell growth.

In an embodiment of the invention, the isolated nucleic acid sequence of the chimeric amino acid encodes an extracellular domain or binding fragment thereof from the ErbB2 receptor, and wherein the multimerization domain comprises an immunoglobulin constant region.

In still another embodiment of the invention, the isolated nucleic acid sequence of the chimeric amino acid sequence encodes an extracellular domain or binding fragment thereof from the ErbB3 receptor ECD, and wherein the multimerization domain comprises an immunoglobulin constant region.

In another embodiment of the invention, the isolated nucleic acid sequence of the chimeric amino acid sequence encodes an extracellular domain or binding fragment thereof from the ErbB4 receptor ECD, and wherein the multimerization domain comprises an immunoglobulin constant region.

Another embodiment of the invention includes a promoter operably linked to the nucleic acid molecule.

In still another embodiment, the invention includes a vector comprising the isolated nucleic acid of the invention. For example, the invention provides a vector comprising the nucleic acid molecule (e.g. an expression vector comprising the nucleic acid molecule operably linked to control sequences recognized by a host cell transformed with the vector); a host cell comprising the nucleic acid molecule; and a method of using a nucleic acid molecule encoding a chimeric heteromultimer adhesin, such as an ErbB-IgG, to effect production of the adhesin which comprises the step of culturing the host cell and recovering the adhesin from the cell culture. In a related embodiment the method of using the nucleic acid to effect production of the adhesin includes introducing multiple nucleic acid sequences encoding different chimeric adhesins and expressing a mixture of chimeric adhesins. For example, a nucleic acid encoding ErbB2-IgG and a nucleic acid encoding ErbB3-IgG are introduced into a host cell, expressed, and a mixture of the homodimers and heterodimer is isolated from the cell or from the culture medium.

An embodiment of the invention further includes a host cell comprising the nucleic acid of the invention. Preferably the host cell is capable of expressing the nucleic acid, which expression includes the translation and production of the chimeric heteroadhesin of the invention. The embodiment of the invention encompasses a host cell comprising and expressing a chimeric monomer of the heteroadhesin, while in another host cell of the invention an additional chimeric monomer of the heteroadhesin is expressed. Alternatively, the embodiment encompasses the expression of more than one chimeric monomer in a single host cell.

In a preferred embodiment of the invention, the host cell comprises a first isolated nucleic acid sequence encoding the first amino acid sequence of the soluble chimeric heteromultimer of the invention, wherein the extracellular domain is from the ErbB2 receptor and wherein the multimerization domain comprises an immunoglobulin constant region; and a second isolated nucleic acid sequence encoding an additional amino acid sequence of the soluble chimeric heteromultimer of the invention, wherein the extracellular domain is from the ErbB3 receptor and wherein the multimerization domain comprises an immunoglobulin constant region.

In another preferred embodiment of the invention, the host cell comprises a first isolated nucleic acid sequence encoding the first amino acid sequence of the soluble chimeric heteromultimer of the invention, wherein the extracellular domain is from the ErbB2 receptor and wherein the multimerization domain comprises an immunoglobulin constant region; and a second isolated nucleic acid sequence encoding an additional amino acid sequence of the soluble chimeric heteromultimer of the invention, wherein the extracellular domain is from the ErbB4 receptor and wherein the multimerization domain comprises an immunoglobulin constant region.

Another aspect of the invention includes an antagonist antibody to the chimeric heteromultimer adhesin of the invention, wherein the antibody binds to the natural heteromultimeric receptor and inhibits its activation.

Another aspect of the invention includes an agonist antibody to the chimeric heteromultimer adhesin of the invention, wherein the antibody binds to the natural heteromultimeric receptor and activates it. In preferred embodiments of the invention, the agonist antibody is capable of activating the natural heteromultimeric receptor at $10^{-1}$ to $10^6$ fold the activity of the natural ligand.

The chimeric heteromultimer-specific antibodies may be used, among other things, in a method for detecting heteromultimeric receptors which comprises the step of contacting a sample suspected of containing the heteromultimeric receptor with the antibody (which is optionally labeled) and detecting if binding has occurred. The antibody may also be used in a method for purifying the heteromultimeric receptor which comprises the step of passing a mixture containing the heteromultimeric receptor over a solid phase to which is bound the antibody and recovering the fraction containing the heteromultimeric receptor. Preferably, in one embodiment of the invention the heteromultimeric receptor is ErbB2/ErbB4 and the chimeric heteromultimer adhesin is ErbB2-IgG/ErbB4-IgG. In another preferred embodiment, the heteromultimeric receptor is ErbB2/ErbB3 and the chimeric heteromultimer adhesin is ErbB2-IgG/ErbB3-IgG.

In yet another aspect, the invention includes a method of forming a chimeric heteromultimer adhesin-ligand complex in a sample comprising the ligand. The method of the invention includes contacting the chimeric heteromultimer adhesin of the invention with the sample under conditions such that the ligand binds to the heteromultimer to form a chimeric heterodimer adhesin-ligand complex.

In an embodiment of the invention, the chimeric heteromultimer adhesin-ligand complex inhibits binding of the ligand to the natural heteromultimer receptor. Preferably the sample is a mammalian tissue or a mammalian fluid, such as a body fluid including, but not limited to blood, serum, plasma, lymph, and urine. Preferably, the mammal is a human.

In another aspect, the invention involves a method of inhibiting natural heteromultimer receptor activation. The method includes the steps of 1) contacting the chimeric heteromultimer adhesin of the invention with a sample containing a ligand for the natural heteromultimeric receptor and the receptor; and 2) incubating the chimeric heteromultimer adhesin with the ligand to form a complex such that activation of the natural heteromultimeric receptor by the ligand is inhibited.

In an embodiment of the method of inhibiting ligand binding to a natural heteromultimer receptor, the natural heteromultimeric receptor is ErbB and the soluble chimeric heteromultimer comprises the extracellular domains of ErbB2 and ErbB3.

In another embodiment of the method of inhibiting ligand binding to a natural heteromultimer receptor, the natural heteromultimeric receptor is ErbB and the soluble chimeric heteromultimer comprises the extracellular domains of ErbB2 and ErbB4.

Another embodiment of the invention is a method of inhibiting ligand binding to a natural heteromultimer receptor, wherein receptor activation is inhibited. The method comprises contacting the antagonist antibody of the invention with the natural heteromultimeric receptor to form an antagonist antibody-heteromultimer receptor complex, wherein activation of the receptor is inhibited.

In another aspect, the invention involves a method of activating a natural heteromultimeric receptor comprising contacting the agonist antibody of the invention with the natural heteromultimeric receptor to form agonist antibody-heteromultimeric receptor complex, wherein the receptor is activated.

In still another aspect, the invention involves a method for the treatment of a disease state comprising administering to a mammal in need thereof a therapeutically effective dose of the chimeric heteromultimer adhesin of the invention. Embodiments of the invention encompass disease states in which the disease is treatable by inhibiting contact between the ligand and the natural heteromultimeric receptor such as by competitive binding of the heteroadhesin to the ligand.

In an embodiment of the invention, the chimeric heteromultimer adhesin is an ErbB2/ErbB3-Ig heteroadhesin. In another embodiment, the chimeric heteromultimer is an ErbB2/ErbB4-Ig heteroadhesin.

The invention encompasses a composition comprising the chimeric heteromultimer adhesin. The composition comprising the adhesin is preferably sterile. Where the composition is an aqueous solution, preferably the adhesin is soluble. Where the composition is a lyophilized powder, preferably the powder is reconstitutable in an appropriate solvent.

In another embodiment of the invention, the treatment method comprises administering chimeric heteromultimer adhesins which comprise chimeric monomers, each prepared using an extracellular domain of the heteromultimeric receptor monomers of interest. The extracellular domains are preferably from receptors selected from the following heteromultimeric receptors: Axl, Rse, epidermal growth factor (EGF) receptor, hepatocyte growth factor (HGF) receptor, IL-2, c-mer, Al-1, EPH, TrkA, TrkB, TrkC, TNF, IL-10, CRF2–4, RXR, RON, AChRα/δ, TRα/RXRα, Trα/DR4, Trα/MHC-TRE, Trα/ME, Trα/F2, KDR/FLT-1, FLT/VEGF, VEGF121/165, Arnt/Ahr, CGA/CGB, EGFR/p185-neu, prolactin receptor (PRL), T cell receptor (TCR), fibroblast growth factor (FGF), and Cak receptor (Kishimoto, T. et al. (1994) Cell 76:253–262; Kendall, R. L., et al. (1996) Biochem Biophys. Res. Comm. 226:324–328; Chang, W.-P. And Clevenger, C. V. (1996) PNAS USA 93:5947–5952; Lala, D. S. et al. (1996) Nature 383:450–453; Collesi, C. et al. (1996) Mol. Cell. Biol. 16:5518–5526; Tzahar, E. et al. (1996) Mol. Cell. Biol. 16:5276–5287; Shtrom, S. S. and Hall, Z. W. (1996) J. Biol. Chem. 271:25506–25514; Nagaya, T. et al. (1996) Biochem. Biophys. Res. Comm. 226:426–430; Dendall, R. L. et al. (1996) Biochem. Biophys. Res. Comm. 226:324–328; Kainu, T. et al. (1995) Neuroreport 6:2557–2560; Yoo, S. H. and Lewis, M. S. (1996) J. Biol. Chem. 271:17041–17046; Murali, R. et al. (1996) PNAS USA 93:6252–6257; Dietrich J. et al. (1996) J. Cell Biol. 132:299–310; Tanahashi, T. et al. (1996) J. Biol. Chem 271:8221–8227; and Perez, J. L. et al. (1996) Oncogene 12:1469–1477). The extracellular domains are more preferably from receptors selected from the following: IL-6/gp130, IL-11/gp130 leukemia inhibitory factor (LIF)/gp130, cardiotrophin-1/gp130 (CT-1), IL-11/gp130, ciliary neurotrophic factor CNTF/gp130, oncostatin M (OSM)/gp130, interferon γ, and interferon α, β (Kishimoto, T. et al. (1994), supra; Taga, T. (1996) J. Neurochem. 67:1–10; Pennica, D. et al. (1995) J. Biol. Chem. 270:10915–10922; Marsters, S. A. (1995) PNAS USA 92:5401–5405; and Wollert, K. C. et al. (1996) J. Biol. Chem. 271:9535–9545). Most preferably, the extracellular domains are selected from the ErbB family of receptors.

Embodiments of the method of treatment encompass a disease state or states such as immunological disorders, cancer, and neurological disorder.

In embodiments where the heteroadhesin is an ErbB2/ErbB3-Ig or an ErbB2/ErbB4-Ig heteroadhesin, the method of treatment encompasses a disease state selected from the group consisting of inflammatory disease, cancer, neurological disorders such as neurofibromatosis and peripheral neuropathy, and cardiac disorders such as cardiac hypertrophy.

The invention further provides a method for treating a mammal comprising administering a therapeutically effective amount of a chimeric heteromultimer adhesin, such as ErbB2/3-IgG or ErbB2/4-IgG to the mammal. For example, the mammal may be suffering from a neurological disorder or cell proliferative disease. The mammal is one which could benefit from a reduction in HRG levels/biological activity (e.g. in cancer).

In another aspect, the invention includes pharmaceutical compositions. In an embodiment of the invention the pharmaceutical composition comprises a chimeric heteromultimer adhesin of the invention, which heteroadhesin 1) comprises an ECD or binding fragment thereof of a natural heteromultimeric receptor, and 2) is an antagonist of the ligand which binds the ECD of the natural heteromultimeric receptor.

In another embodiment of the invention the pharmaceutical composition comprises an antibody to a chimeric heteromultimer adhesin of the invention, which anti-heteroadhesin antibody 1) comprises an ECD or binding fragment thereof of a natural heteromultimeric receptor, and 2) binds to the ECD of the natural heteromultimeric receptor and is an antagonist of the ligand which binds the ECD of the natural heteromultimeric receptor.

In still another embodiment of the invention the pharmaceutical composition comprises an antibody to a chimeric heteromultimer adhesin of the invention, which anti-heteroadhesin antibody 1) comprises and ECD or binding fragment thereof of a natural heteromultimeric receptor, and 2) binds to the ECD of the natural heteromultimeric receptor and is an agonist of the ligand which binds the ECD of the natural heteromultimeric receptor.

In yet another aspect, the invention includes articles of manufacture comprising a container, a label on the container, and a composition contained within the container. In one embodiment of the invention, the composition comprises the chimeric heteromultimer adhesin composition of the invention, which heteroadhesin is an antagonist of ligand. The composition is effective for antagonizing binding of the ligand to its natural heteromultimeric receptor, and the label on the container indicates that the composition can be used for antagonizing binding of the ligand to the natural heteromultimeric receptor. In a preferred embodiment the chimeric heteromultimer adhesin is selected from the group consisting of ErbB2/ErbB3-Ig or ErbB2/ErbB4-Ig.

In another embodiment of the article of manufacture, the composition comprises an anti-chimeric heteromultimer adhesin antibody, which antibody is an antagonist of a ligand. The composition is effective for antagonizing binding of the ligand to its natural heteromultimeric receptor, and the label on the container indicates that the composition can be used for antagonizing binding of the ligand to the natural heteromultimeric receptor. In a preferred embodiment the anti-chimeric heteromultimer adhesin antibody is an antibody raised to a chimeric heteroadhesin selected from the group consisting of ErbB2/ErbB3-Ig or ErbB2/ErbB4-Ig.

In yet another embodiment of the article of manufacture, the composition comprises an anti-chimeric heteromultimer adhesin antibody, which antibody is an agonist of a ligand. The composition is effective for activating the natural heteromultimeric receptor of the ligand, and the label on the container indicates that the composition can be used for activating the natural heteromultimeric receptor. In a preferred embodiment the anti-chimeric heteromultimer adhesin antibody is an antibody raised to a chimeric heteroadhesin selected from the group consisting of ErbB2/ErbB3-Ig or ErbB2/ErbB4-Ig.

These and other aspects of the invention will be apparent to those skilled in the art upon consideration of the following detailed description.

BRIEF DESCRIPTION OF THE DRAWINGS

As shown in FIG. 3A, a high affinity HRG binding site could be detected with the ErbB2-containing heterodimers but not the ErbB3/4-IgG.

DETAILED DESCRIPTION

Figure 1:
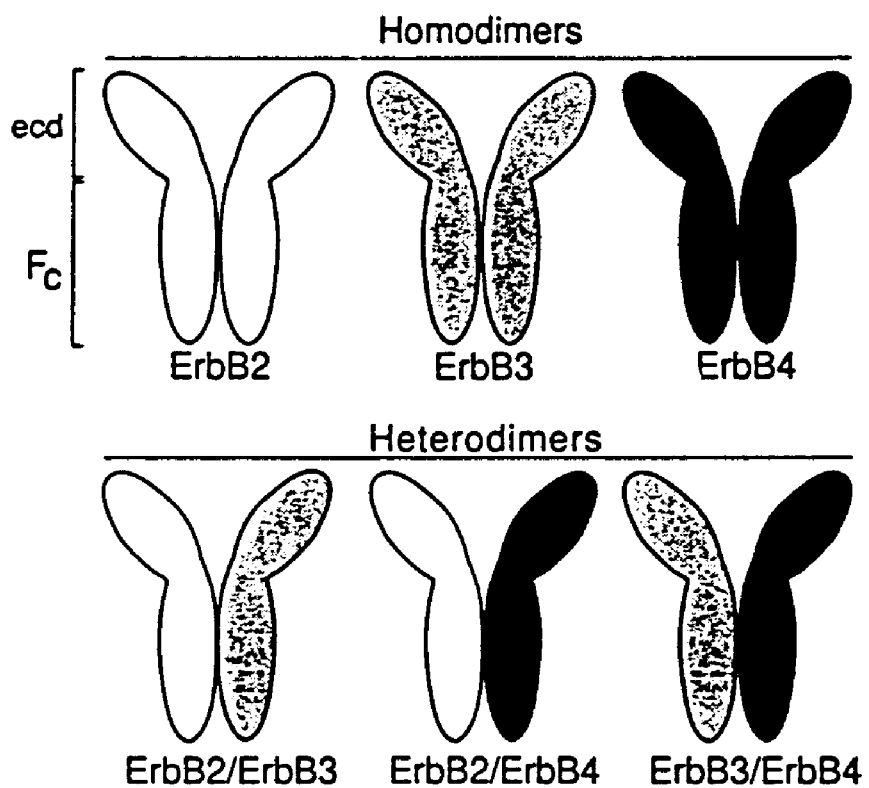
FIG. 1 is a diagram of the ErbB family of chimeric homodimers and heterodimers. The extracellular domains (ECD) and immunoglobulin region (Fc) of the chimeras are indicated. The extracellular domains are derived from the natural heteromultimeric receptor and are fused by recombinant means to a multimerization domain, the immunoglobulin region.

Before the present chimeric heteromultimer adhesins, methods of making them, and uses therefor are described, it is to be understood that this invention is not limited to the particular adhesins or processes described as such compounds and methods may, of course, vary. It is also to be understood that the terminology used herein is for the purpose of describing particular embodiments only, and is not intended to be limiting since the scope of the present invention will be limited only by the appended claims.

I. Definitions

In general, the following words or phrases have the indicated definition when used in the description, examples, and claims.

Unless indicated otherwise, the term "ErbB" when used herein refers to any one or more of the mammalian ErbB receptors (i.e. ErbB1 or epidermal growth factor (EGF) receptor; ErbB2 or HER2 receptor; ErbB3 or HER3 receptor; ErbB4 or HER4 receptor; and any other member(s) of this class I tyrosine kinase family to be identified in the future) and "erbB" refers to the mammalian erbB genes encoding these receptors.

"HRG" (or "heregulin") is defined herein to be any polypeptide sequence that possesses at least one biological property (as defined below) of native sequence HRG (U.S. application Ser. No. 60/021,640, PR1043, supra). This definition encompasses not only the polypeptide isolated from a native HRG source such as human MDA-MB-175 cells or from another source, such as another animal species, but also the polypeptide prepared by recombinant or synthetic methods. It also includes variant forms including functional derivatives, allelic variants, naturally occurring isoforms and analogues thereof. Sometimes the HRG is "native HRG" which refers to endogenous HRG polypeptide which has been isolated from a mammal. The HRG can also be "native sequence HRG" insofar as it has the same amino acid sequence as a native HRG (e.g. human HRG). However, "native sequence HRG" encompasses the polypeptide produced by recombinant or synthetic means. "Mature HRG" is soluble or secreted HRG released from the cell (i.e. lacking amino-terminal sequence). HRG "isoforms" are naturally occurring polypeptides which comprise at least part of the N-terminal domain of HRG.

The term "immunoadhesin" as used herein refers to antibody-like molecules which combine the binding domain of a protein such as an extracellular domain (the adhesin portion) of a cell-surface receptor with the effector functions of an immunoglobulin constant domain. Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use.

Immunoadhesins reported in the literature include fusions of the T cell receptor (Gascoigne et al., Proc. Natl. Acad. Sci. USA 84:2936–2940 (1987)); CD4 (Capon et al., Nature 337:525–531 (1989); Traunecker et al., Nature 339:68–70

(1989); Zettmeissl et al., DNA Cell Biol. USA 9:347–353 (1990); and Byrn et al., Nature 344:667–670 (1990)); L-selectin or homing receptor (Watson et al., J. Cell. Biol. 110:2221–2229 (1990); and Watson et al., Nature 349:164–167 (1991)); CD44 (Aruffo et al., Cell 61:1303–1313 (1990)); CD28 and B7 (Linsley et al., J. Exp. Med. 173:721–730 (1991)); CTLA-4 (Lisley et al., J. Exp. Med. 174:561–569 (1991)); CD22 (Stamenkovic et al., Cell 66:1133–1144 (1991)); TNF receptor (Ashkenazi et al., Proc. Natl. Acad. Sci. USA 88:10535–10539 (1991); Lesslauer et al., Eur. J. Immunol. 27:2883–2886 (1991); and Peppel et al., J. Exp. Med. 174:1483–1489 (1991)); NP receptors (Bennett et al., J. Biol. Chem. 266:23060–23067 (1991)); inteferon γ receptor (Kurschner et al., J. Biol. Chem. 267:9354–9360 (1992)); 4–1BB (Chalupny et al., PNAS USA 89:10360–10364 (1992)) and IgE receptor α (Ridgway and Gorman, J. Cell. Biol. 115, Abstract No. 1448 (1991)).

Examples of homomultimeric immunoadhesins which have been described for therapeutic use include the CD4-IgG immunoadhesin for blocking the binding of HIV to cell-surface CD4. Data obtained from Phase I clinical trials in which CD4-IgG was administered to pregnant women just before delivery suggests that this immunoadhesin may be useful in the prevention of maternal-fetal transfer of HIV. Ashkenazi et al., Intern. Rev. Immunol. 10:219–227 (1993). An immunoadhesin which binds tumor necrosis factor (TNF) has also been developed. TNF is a proinflammatory cytokine which has been shown to be a major mediator of septic shock. Based on a mouse model of septic shock, a TNF receptor immunoadhesin has shown promise as a candidate for clinical use in treating septic shock (Ashkenazi, A. et al. (1991) PNAS USA 88:10535–10539). Immunoadhesins also have non-therapeutic uses. For example, the L-selectin receptor immunoadhesin was used as a reagent for histochemical staining of peripheral lymph node high endothelial venules (HEV). This reagent was also used to isolate and characterize the L-selectin ligand (Ashkenazi et al., supra).

If the two arms of the immunoadhesin structure have different specificities, the immunoadhesin is called a "bispecific immunoadhesin" by analogy to bispecific antibodies. Dietsch et al., J. Immunol. Methods 162:123 (1993) describe such a bispecific immunoadhesin combining the extracellular domains of the adhesion molecules, E-selectin and P-selectin, each of which selectins is expressed in a different cell type in nature. Binding studies indicated that the bispecific immunoglobulin fusion protein so formed had an enhanced ability to bind to a myeloid cell line compared to the monospecific immunoadhesins from which it was derived.

The term "heteroadhesin" is used interchangeably with the expression "chimeric heteromultimer adhesin" and refers to a complex of chimeric molecules (amino acid sequences) in which each chimeric molecule combines a biologically active portion, such as the extracellular domain of each of the heteromultimeric receptor monomers, with a multimerization domain. The "multimerization domain" promotes stable interaction of the chimeric molecules within the heteromultimer complex. The multimerization domains may interact via an immunoglobulin sequence, leucine zipper, a hydrophobic region, a hydrophilic region, or a free thiol which forms an intermolecular disulfide bond between the chimeric molecules of the chimeric heteromultimer. The multimerization domain may comprise an immunoglobulin constant region. A possible multimerization domain useful in the present invention is found in U.S. application Ser. No. 07/440,625, P565P1 (herein incorporated by reference) in which hybrid immunoglobulins are described. In addition a multimerization region may be engineered such that steric interactions not only promote stable interaction, but further promote the formation of heterodimers over homodimers from a mixture of monomers. See, for example, U.S. application Ser. No. 08/399,106, P0927 (herein incorporated by reference in its entirety) in which a "protuberance-into-cavity" strategy is disclosed for an interface between a first and second polypeptide for hetero-oligomerization. "Protuberances" are constructed by replacing small amino acid side chains from the interface of the first polypeptide with larger side chains (e.g. tyrosine or tryptophan). Compensatory "cavities" of identical or similar size to the protuberances are optionally created on the interface of the second polypeptide by replacing large amino acid side chains with smaller ones (e.g. alanine or threonine). The immunoglobulin sequence preferably, but not necessarily, is an immunoglobulin constant domain. The immunoglobulin moiety in the chimeras of the present invention may be obtained from $IgG_1$, $IgG_2$, $IgG_3$ or $IgG_4$ subtypes, IgA, IgE, IgD or IgM, but preferably $IgG_1$ or $IgG_3$. The term "epitope tagged" when used herein refers to a chimeric polypeptide comprising the entire chimeric heteroadhesin, or a fragment thereof, fused to a "tag polypeptide". The tag polypeptide has enough residues to provide an epitope against which an antibody can be made, yet is short enough such that it does not interfere with activity of the chimeric heteroadhesin. The tag polypeptide preferably is fairly unique so that the antibody thereagainst does not substantially cross-react with other epitopes. Suitable tag polypeptides generally have at least 6 amino acid residues and usually between about 8–50 amino acid residues (preferably between about 9–30 residues). An embodiment of the invention encompasses a chimeric heteroadhesin linked to an epitope tag, which tag is used to detect the adhesin in a sample or recover the adhesin from a sample.

"Isolated chimeric heteromultimer adhesin", "highly purified chimeric heteromultimer adhesin" and "substantially homogeneous chimeric heteromultimer adhesin" are used interchangeably and mean the adhesin that has been purified from a source or has been prepared by recombinant or synthetic methods and is sufficiently free of other peptides or proteins to homogeneity by chromatographic techniques or other purification techniques, such as SDS-PAGE under non-reducing or reducing conditions using Coomassie blue or, preferably, silver stain. Homogeneity here means less than about 5% contamination with other source proteins. As disclosed herein (below), the ErbB2/3-IgG or ErbB2/4-IgG chimeric heteroadhesins of the invention bind with sufficiently greater affinity relative to the homodimers that the use of a mixture of homodimers and heterodimers is also considered a useful embodiment of the invention. The terms "chimeric heteromultimer adhesin", "chimeric heteroadhesin" and "CHA" are used interchangeably herein.

"Biological property" when used in conjunction with "chimeric heteromultimer adhesin" means an ability to bind a ligand and function as an antagonist of the ligand for binding to the natural receptor. "Biological property" when used in conjunction with "an antibody to a chimeric heteromultimer adhesin" means an ability to bind the extracellular domains encoded in the adhesin or the extracellular domains of the natural heteromultimeric receptor such that the antibody acts as an antagonist or an agonist of the ligand.

"Biological activity" where used in conjunction with a chimeric heteroadhesin such as the ErbB heteroadhesins includes functioning as an antagonist of heregulin receptor activation (e.g. antagonizing activation of the ErbB2, ErbB3 and/or ErbB4 receptor) by binding to cell membrane associated heregulin or secreted heregulin; inhibition of growth of cells expressing ErbB receptors on their surface; inhibition of differentiation and/or proliferation of cells expressing these receptors (e.g. SK-BR-3 cells, Schwann cells, hepatocytes, glioblastoma cells, epithelial cells (such as in breast, ovary, prostate, lung, pancreas, colon and rectum), muscle cells, astrocytes and/or oligodendrocytes); inhibition of receptor binding (e.g. to the ErbB2/3, ErbB2/4, ErbB3 and/or ErbB4 receptor); inhibition of mitogenic activity; inhibiting acetylcholine receptor synthesis at the neuromuscular junction; and inhibiting formation of a synaptic junction between a neuron and a muscle, nerve or glandular cell.

"Biological activity" where used in conjunction with an agonist chimeric heteroadhesin antibody such as an agonist anti-ErbB heteroadhesins antibody include functioning as an agonist of heregulin receptor activation (e.g. activation of the ErbB2, ErbB3 and/or ErbB4 receptor); receptor binding and activation(e.g. to the ErbB2/3, ErbB2/4, ErbB3 and/or ErbB4 receptor); promoting growth of cells expressing ErbB receptors on their surface; promoting differentiation and/or proliferation of cells expressing these receptors (e.g. SK-BR-3 cells, Schwann cells, hepatocytes, glioblastoma cells, epithelial cells (such as in breast, ovary, prostate, lung, pancreas, colon and rectum), muscle cells, astrocytes and/or oligodendrocytes); promoting mitogenic activity; promoting acetylcholine receptor synthesis at the neuromuscular junction; and promoting formation of a synaptic junction between a neuron and a muscle, nerve or glandular cell.

"Percent amino acid sequence identity" with respect to the chimeric heteromultimer adhesin is defined herein as the percentage of amino acid residues in the candidate extracellular domain sequence that are identical with the residues in the extracellular domain sequence of a monomer of the natural heteromultimeric receptor, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the adhesin sequence shall be construed as affecting sequence identity or homology.

The term "disease state" refers to a physiological state of a cell or of a whole mammal in which an interruption, cessation, or disorder of cellular or body functions systems, or organs has occurred.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer. Where the chimeric heteroadhesin of the invention in an ErbB-Ig heteroadhesin, the cancer to be treated is preferably cancerous growth of cells expressing the ErbB receptors, such as cancerous growth of breast, ovary, prostate, lung, pancreas, and colorectal cells.

The term "inflammatory disorder" referes to a fundamental pathologic process consisting of a dynamic complex of cytologic and histologic reactions that occur in the affected blood vessels and adjacent tissues in response to an injury or abnormal stimulation caused by a physical, chemical, or biologic agent, including: 1) the local reactions and resulting morphologic changes, 2) the destruction or removal of the injurious material, 3) the responses that lead to repair and healing. Inflammatory disorders treatable by the invention are those wherein the inflammation is associated with cytokine-induced disorders, such as those associated with interleukin and leukemia inhibitory factor cytokines. Such disorders include abnormalities in thrombopoiesis, macrophage growth and differentiation, proliferation of hematopoietic progenitors, and the like.

The term "neurological disorder" refers to or describes the physiological condition in mammals that is typically characterized by nerve cell growth, differentiation, or cell signalling. Examples of neurological disorders include, but are not limited to, neurofibromatosis and peripheral neuropathy.

The term "cardiac disorder" refers to or describes the physiological condition in mammals that is typically characterized by cardiac cell growth and differentiation. An example of a cardiac disorder includes, but is not limited to, cardiac hypertrophy and heart failure, including congestive heart failure, myocardial infarction, and tachyarrhythmia. "Heart failure" refers to an abnormality of cardiac function where the heart does not pump blood at the rate needed for the requirements of metabolizing tissues.

"Determining disease status" refers to the act of determining likelihood of patient survival and time to relapse for neoplastic diseases, particularly breast, ovarian, stomach, endometrial, salivary gland, lung, kidney, colon, and bladder carcinomas. In particular, an antibody of the invention (raised to the chimeric heteroadhesin of the invention and capable of interacting with the extracellular domains) can be used to quantify the heteromultimeric receptor (e.g., ErbB2, ErbB3 or ErbB4, but normally ErbB2) overexpression in cancerous tissue taken from a patient suffering from carcinoma. This can also be referred to as "determining the proper course of treatment for patients suffering from cancer". For example, those patients characterized by ErbB2 overexpression or having increased amounts of ErbB2/3 or ErbB2/4 cell surface receptors may require more aggressive treatment (e.g. high doses of chemo- or radiotherapy treatment) than might otherwise be indicated by other diagnostic factors. This phrase encompasses diagnosing patients suffering from high grade ductal carcinoma in situ, including extensive intraductal carcinoma. See, e.g., Disis et al., Cancer Research, 54:16–20 (1994).

The word "sample" refers to tissue, body fluid, or a cell from a patient. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues will be obtained and appropriately prepared. Other patient samples, including urine, tear drops, serum, cerebrospinal fluid, feces, sputum, cell extracts etc. will also be useful for particular tumors.

The expression "labeled" when used herein refers to a molecule (e.g. a chimeric heteroadhesin such as ErbB2/3-IgG) which has been conjugated, directly or indirectly, with a detectable compound or composition. The label may be detectable by itself (e.g. radioisotope labels or fluorescent labels) or, in the case of an enzymatic label, may catalyze a chemical alteration of a substrate compound or composition which is detectable.

By "solid phase" is meant a non-aqueous matrix to which a reagent of interest (e.g., ErbB2/3-IgG, ErbB2/4-IgG or an antibody thereto) can adhere. Examples of solid phases encompassed herein include those formed partially or entirely of glass (e.g.,controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

The phrase "activating an ErbB receptor" refers to the act of causing the intracellular kinase domain of an ErbB receptor to phosphorylate tyrosine residues. Generally, this will involve binding of an antibody raised to ErbB2/3-Ig, for example, which antibody is tested for its ability to act as an agonist of heregulin by binding to a receptor complex of two or more ErbB receptors (e.g., an ErbB2/ErbB3 or ErbB2/ErbB4 complex) which activates a kinase domain of one or more of those receptors and thereby results in phosphorylation of tyrosine residues in one or more of the receptors, and/or phosphorylation of tyrosine residues in additional substrate polypeptides(s). ErbB receptor phosphorylation can be quantified using the tyrosine phosphorylation assays described below. The phrase "inhibiting an ErbB receptor" refers to the antagonistic property of a chimeric ErbB heteroadhesin or an antagonist antibody raised against it which, when bound to an ErbB receptor prevents activation of the receptor (i.e. inhibits kinase function).

The expression "decreasing survival of a cell" refers to the act of decreasing the period of existence of a cell, relative to an untreated cell which has not been exposed to chimeric ErbB-IgG (or an antagonistic antibody raised thereto) either in vitro or in vivo. The expression "decreased cell proliferation" refers to a decrease in the number of cells in a population exposed to chimeric ErbB-IgG (or an antagonistic antibody raised thereto) either in vitro or in vivo, relative to an untreated cell.

The expression "increasing survival of a cell" or "increased cell proliferation" refers to increased existence or increased number of cells in a population exposed to an agonist antibody raised to a chimeric ErbB-IgG of the invention, either in vitro or in vivo, relative to an untreated cell. An increase or decrease in cell proliferation in cell culture can be detected by counting the number of cells before and after exposure to the agonist anti-ErbB-IgG antibody. The extent of proliferation can be quantified via microscopic examination of the degree of confluency. Cell proliferation can also be quantified by measuring $^3$H-thymidine uptake by the cells.

By "enhancing differentiation of a cell" is meant the act of increasing the extent of the acquisition or possession of one or more characteristics or functions which differ from that of the original cell (i.e. cell specialization). This can be detected by screening for a change in the phenotype of the cell (e.g. identifying morphological changes in the cell). Enhancing differentiation of a cell also refers herein to cellular maturation in which, for example, unique proteins associated with the mature cell are synthesized.

A "glial cell" is derived from the central and peripheral nervous system and can be selected from oligodendroglial, astrocyte, ependymal, or microglial cells as well as satellite cells of ganglia and the neurolemmal cells around peripheral nerve fibers.

"Muscle cells" include skeletal, cardiac or smooth muscle tissue cells. This term encompasses those cells which differentiate to form more specialized muscle cells (e.g. myoblasts).

"Isolated nucleic acid" is RNA or DNA free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by nucleic acid sequences not normally found in the source cell. Isolated nucleic acid is RNA or DNA that encodes a biologically active chimeric heteromultimer adhesin in which each extracellular domain shares at least 75%, more preferably at least 80%, still more preferably at least 85%, even more preferably 90%, and most preferably 95% sequence identity with the extracellular domain of the monomer of the natural receptor from which it was derived.

"Stringent conditions" are those that (a) employ low ionic strength and high temperature for washing, for example, 0.015 M NaCl/0.0015 M sodium citrate/0.1% NaDodSO$_4$ (SDS) at 50° C., or (b) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/mL), 0.1% SDS, and 10% dextran sulfate at 42° C., with washes at 42° C. in 0.2×SSC and 0.1% SDS.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc., as necessary to accommodate factors such as probe length and the like. The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

An HRG "antagonist" is a molecule which prevents, or interferes with, an HRG effector function (e.g. a molecule which prevents or interferes with binding and/or activation of an ErbB receptor by HRG). Such molecules can be screened for their ability to competitively inhibit ErbB receptor activation by HRG in the tyrosine phosphorylation assay disclosed herein, for example. Preferred antagonists are those which do not substantially interfere with the interaction of other heregulin polypeptides with ErbB receptor(s). Examples of HRG antagonists include neutralizing antibodies against ErbB2/3-Ig or ErbB2/4-Ig chimeric heteroadhesins of the invention.

The term "antibody" is used in the broadest sense and specifically covers single anti-chimeric heteroadhesin (such as anti-ErbB2/3-IgG or anti-ErbB2/4-IgG) monoclonal antibodies and anti-chimeric heteroadhesin antibody compositions with polyepitopic specificity (including neutralizing and non-neutralizing antibodies). The antibody of particular interest herein is one which does not significantly cross-react with other heteromultimer receptors, such as those described in the background section above and thus is one which "binds specifically" to a heteromultimer receptor, such as ErbB2/3 or ErbB2/4. In such embodiments, the extent of binding of the antibody to non-ErbB receptors will be less than 10% as determined by radioimmunoprecipitation (RIA), for example.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-chimeric heteroadhesin antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab)$_2$, and Fv), so long as they exhibit the desired biological activity. (See, e.g., U.S. Pat. No. 4,816,567 and Mage & Lamoyi, in *Monoclonal Antibody Production Techniques and Applications*, pp.79–97 (Marcel Dekker, Inc.), New York (1987)).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, Nature 256:495 (1975), or may be made by recombinant DNA methods (U.S. Pat. No. 4,816,567). The "monoclonal antibodies" may also be isolated from phage libraries generated using the techniques described in McCafferty et al., Nature 348:552–554 (1990), for example.

"Humanized" forms of non-human (e.g. murine) antibodies are specific chimeric immunoglobulins, immunoglobulin chains or fragments thereof (such as Fv, Fab, Fab', F(ab)$_2$ or other antigen-binding subsequences of antibodies) which contain minimal sequence derived from non-human immunoglobulin. For the most part, humanized antibodies are human immunoglobulins (recipient antibody) in which residues from the complementarity determining regions (CDRs) of the recipient antibody are replaced by residues from the CDRs of a non-human species (donor antibody) such as mouse, rat or rabbit having the desired specificity, affinity and capacity. In some instances, Fv framework region (FR) residues of the human immunoglobulin are replaced by corresponding non-human FR residues. Furthermore, the humanized antibody may comprise residues which are found neither in the recipient antibody nor in the imported CDR or FR sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR residues are those of a human immunoglobulin consensus sequence. The humanized antibody optimally also will comprise at least a portion of an immunoglobulin constant region (Fc), typically that of a human immunoglobulin.

By "neutralizing antibody" is meant an antibody molecule as herein defined which is able to block or significantly reduce an effector function of native sequence HRG. For example, a neutralizing antibody may inhibit or reduce the ability of HRG to activate an ErbB receptor in the tyrosine phosphorylation assay described herein. The neutralizing antibody may also block the mitogenic activity of HRG in the cell proliferation assay disclosed herein.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as sheep, dogs, horses, cats, cows, etc. Preferably, the mammal herein is human.

"Pharmaceutically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, polyethylene glycol (PEG), and Pluronics™.

II. Modes for Practicing the Invention

1. Production of a Chimeric Heteromultimer Adhesin

A chimeric heteroadhesin of the invention is preferably produced by expression in a host cell and isolated therefrom. A host cell is generally transformed with the nucleic acid of the invention. Preferably the nucleic acid is incorporated into an expression vector. Suitable host cells for cloning or expressing the vectors herein are prokaryote host cells (such as *E. coli*, strains of Bacillus, Pseudomonas and other bacteria), yeast and other eukaryotic microbes, and higher eukaryote cells (such as Chinese hamster ovary (CHO) cells and other mammalian cells). The cells may also be present in live animals (for example, in cows, goats or sheep). Insect cells may also be used. Cloning and expression methodologies are well known in the art.

To obtain expression of a chimeric heteromultimer such as ErbB2-IgG, ErbB3-IgG, and/or ErbB4-IgG, an expression vector is introduced into host cells by transformation or transfection and the resulting recombinant host cells are cultured in conventional nutrient media, modified as appropriate for inducing promoters, selecting recombinant cells, or amplifying ErbB-IgG DNA. In general, principles, protocols, and practical techniques for maximizing the productivity of in vitro mammalian cell cultures can be found in *Mammalian Cell Biotechnology: a Practical Approach*, M. Butler, ed. (IRL Press, 1991).

The terms "transformation" and "transfection" are used interchangeably herein and refer to the process of introducing DNA into a cell. Following transformation or transfection, the nucleic acid of the invention may integrate into the host cell genome, or may exist as an extrachromosomal element. If prokaryotic cells or cells that contain substantial cell wall constructions are used as hosts, the preferred methods of transfection of the cells with DNA is the calcium treatment method described by Cohen, S. N. et al., Proc. Natl. Acad. Sci. U.S.A., 69:2110–2114 (1972) or the polyethylene glycol method of Chung et al., Nuc. Acids. Res. 16:3580 (1988). If yeast are used as the host, transfection is generally accomplished using polyethylene glycol, as taught by Hinnen, Proc. Natl. Acad. Sci. U.S.A., 75:1929–1933 (1978). If mammalian cells are used as host cells, transfection generally is carried out by the calcium phosphate precipitation method, Graham et al., Virology 52:546 (1978), Gorman et al., DNA and Protein Eng. Tech 2:3–10 (1990). However, other known methods for introducing DNA into prokaryotic and eukaryotic cells, such as nuclear injection, electroporation, or protoplast fusion also are suitable for use in this invention.

Particularly useful in this invention are expression vectors that provide for the transient expression in mammalian cells of DNA encoding a chimeric heteroadhesin such as ErbB2/3-Ig or ErbB2/4-Ig. In general, transient expression involves the use of an expression vector that is able to efficiently replicate in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

A chimeric heteroadhesin preferably is recovered from the culture medium as a secreted polypeptide, although it also may be recovered from host cell lysates. As a first step, the particulate debris, either host cells or lysed fragments, is removed, for example, by centrifugation or ultrafiltration; optionally, the protein may be concentrated with a commercially available protein concentration filter, followed by separating the chimeric heteroadhesin from other impurities by one or more purification procedures selected from: fractionation on an immunoaffinity column; fractionation on an ion-exchange column; ammonium sulphate or ethanol precipitation; reverse phase HPLC; chromatography on silica; chromatography on heparin Sepharose; chromatography on a cation exchange resin; chromatofocusing; SDS-PAGE; and gel filtration.

Preparation of epitope tagged chimeric heteromultimer, such as ErbB-IgG, facilitates purification using an immunoaffinity column containing antibody to the epitope to adsorb the fusion polypeptide. Immunoaffinity columns such as a rabbit polyclonal anti-ErbB column can be employed to absorb the ErbB-IgG by binding it to an ErbB immune epitope.

Amino acid sequence variants of native sequence extracellular domain included in the chimeric heteroadhesin are prepared by introducing appropriate nucleotide changes into the native extracellular domain DNA sequence, or by in vitro synthesis of the desired chimeric heteroadhesin monomer polypeptide. Such variants include, for example, deletions from, or insertions or substitutions of, residues in the amino acid sequence of the chimeric heteroadhesin.

Variations in the native sequence as described above can be made using any of the techniques and guidelines for conservative and non-conservative mutations set forth in U.S. Pat. No. 5,364,934. See especially Table 1 therein and the discussion surrounding this table for guidance on selecting amino acids to change, add, or delete.

Nucleic acid molecules encoding amino acid sequence variants of native sequence extracellular domains (such as from ErbB) are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of native sequence ErbB2, -3, and/or -4.

A preferred type of chimeric amino acid sequence is a fusion protein comprising an extracellular domain, such as from an ErbB monomer, linked to a heterologous polypeptide, such as a multimerization domain (immunoglobulin constant region and the like). Such a sequence can be constructed using recombinant DNA techniques. Alternatively, the heterologous polypeptide can be covalently bound to the extracellular domain polypeptide by techniques well known in the art such as the use of the heterobifunctional crosslinking reagents. Exemplary coupling agents include N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

In one embodiment, a chimeric heteroadhesin polypeptide comprises a fusion of a monomer of the chimeric heteroadhesin with a tag polypeptide which provides an epitope to which an anti-tag antibody can selectively bind. Such epitope tagged forms of the chimeric heteroadhesin are useful, as the presence thereof can be detected using a labeled antibody against the tag polypeptide. Also, provision of the epitope tag enables the chimeric heteroadhesin to be readily purified by affinity purification using the anti-tag antibody. Tag polypeptides and their respective antibodies are well known in the art. Examples include the flu HA tag polypeptide and its antibody 12CA5, (Field et al., Mol. Cell. Biol. 8:2159–2165 (1988)); the c-myc tag and the 8F9, 3C7, 6E10, G4, B7 and 9E10 antibodies thereto (Evan et al., Molecular and Cellular Biology 5(12):3610–3616 (1985)); and the Herpes Simplex virus glycoprotein D (gD) tag and its antibody (Paborsky et al., Protein Engineering 3(6):547–553 (1990)).

When preparing the chimeric heteroadhesins of the present invention, nucleic acid encoding an extracellular domain of a natural heteromultimeric receptor is fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The resultant DNA fusion construct is expressed in appropriate host cells.

Another type of covalent modification of a chimeric heteromultimer comprises linking a monomer polypeptide of the heteromultimer to one of a variety of nonproteinaceous polymers, e.g., polyethylene glycol, polypropylene glycol, polyoxyalkylenes, or copolymers of polyethylene glycol and polypropylene glycol. A chimeric heteromultimer also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

Generally, the ErbB chimeric heteromultimers of the invention will have any one or more of the following properties: (a) the ability to compete with a natural heteromultimeric receptor for binding to a neuregulin, such as heregulin; (b) the ability to form ErbB2-IgG/ErbB3-IgG and/or ErbB2-IgG/ErbB4-IgG complexes; and (c) the ability to inhibit activation of a natural heteromultimeric receptor by depleting heregulin from the environment of the natural receptor, thereby inhibiting proliferation of cells that express the ErbB2 and ErbB3 receptor and/or the ErbB2 and ErbB4 receptor.

To screen for property (a), the ability of the chimeric ErbB heteromultimer adhesin to bind to γ-heregulin can be readily determined in vitro. For example, immunoadhesin forms of these receptors can be generated (see below) and the ErbB2/3-Ig or ErbB2/4-Ig heteroimmunoadhesin can be immobilized on a solid phase (e.g. on assay plates coated with goat-anti-human antibody). The ability of HRG to bind to the immobilized immunoadhesin can then be determined, e.g. by determining competitive displacement by other heregulin molecules. For more details, see the $^{125}$I-HRG binding assay described in the Example below.

As to property (c), the tyrosine phosphorylation assay using MCF7 cells described in the Example provides a means for screening for activation of ErbB receptors. In an alternative embodiment of the invention, the KIRA-ELISA described in WO 95/14930 can be used to qualitatively and quantitatively measure the ability of an ErbB chimeric heteroadhesin to inhibit activation of an ErbB receptor.

The ability of a chimeric heteroadhesin such as ErbB2/3-Ig or ErbB2/4-Ig to stimulate proliferation of a cell which expresses the ErbB2 and ErbB3 receptor and/or ErbB2 and ErbB4 receptor can readily be determined in cell culture. Useful cells for this experiment include MCF7 and SK-BR-3 cells obtainable from the ATCC and Schwann cells (see, for example, Li et al., J. Neuroscience 16(6):2012–2019 (1996)). These tumor cell lines may be plated in cell culture plates and allowed to adhere thereto. The HRG ligand in the presence and absence of an ErbB chimeric heteroadhesin is added. Monolayers may be washed and stained/fixed with crystal violet. Cell proliferation or growth inhibition can therefore be quantified as described.

Other heteromultimeric receptors to which the present invention may be applied for the preparation of useful chimeric heteroadhesins include the following: Axl, Rse, epidermal growth factor (EGF) receptor, hepatocyte growth factor (HGF) receptor, IL-2, c-mer, A1-1, EPH, TrkA, TrkB, TrkC, TNF, IL-10, CRF2–4, RXR, RON, AChRα/δ, TRα/RXRα, Trα/DR4, Trα/MHC-TRE, Trα/ME, Trα/F2, KDR/FLT-1, FLT/VEGF, VEGF121/165, Arnt/Ahr, CGA/CGB, EGFR/p185-neu, prolactin receptor (PRL), T cell receptor (TCR), fibroblast growth factor (FGF), Cak receptor, IL-6/gp130, IL-11/gp130 leukemia inhibitory factor (LIF)/gp130, cardiotrophin-1/gp130 (CT-1), IL-11/gp130, ciliary neurotrophic factor CNTF/gp130, oncostatin M (OSM)/gp130, interferon γ, and interferon α, β.

A chimeric heteroadhesin of the invention comprises the extracellular domains of a naturally occurring heteromultimeric receptor, wherein an ECD (or ligand binding fragment thereof) of a monomer of the receptor is fused to a multimerization domain as described above. The chimeric monomers of the heteroadhesin stably associated via the multimerization domains to form the chimeric heteroadhesin. The heteroadhesins of the invention bind the ligand of the natural receptor from which the ECDs are obtained and are useful as antagonists of the ligand. Such antagonists are useful in treating disease states resulting from ligand binding and activation of the natural heteromultimeric receptor.

2. Therapeutic Compositions and Methods

Use of the chimeric heteroadhesins of the invention as therapeutic compositions is an embodiment of the invention. The uses generally disclosed herein are provided as guidance for the use of the chimeric heteroadhesins in general. The ErbB chimeric heteroadhesins are disclosed as examples for further guidance.

HRG promotes the development, maintenance, and/or regeneration of neurons in vivo, including central (brain and spinal chord), peripheral (sympathetic, parasympathetic, sensory, and enteric neurons), and motor neurons. Accordingly, an HRG agonist such as an anti-ErbB-Ig antibody agonist may be utilized in methods for the diagnosis and/or treatment of a variety of "neurologic diseases or disorders" which Affect the nervous system of a mammal, such as a human. According to this embodiment of the invention, the agonist antibody raised to the ErbB chimeric heteroadhesin cross-reacts with and activates the ErbB receptor.

Such diseases or disorders may arise in a patient in whom the nervous system has been damaged by, e.g., trauma, surgery, stroke, ischemia, infection, metabolic disease, nutritional deficiency, malignancy, or toxic agents. The agent is designed to promote the survival, proliferation or differentiation of neurons. For example, anti-ErbB chimeric heteroadhesin agonist antibody can be used to promote the survival or proliferation of motor neurons that are damaged by trauma or surgery. It can also be used to treat motoneuron disorders, such as amyotrophic lateral sclerosis (Lou Gehrig's disease), Bell's palsy, and various conditions involving spinal muscular atrophy, or paralysis. The agonist antibody can be used to treat human "neurodegenerative disorders", such as Alzheimer's disease, Parkinson's disease, epilepsy, multiple sclerosis, Huntington's chorea, Down's Syndrome, nerve deafness, and Meniere's disease.

Further, an anti-ErbB chimeric heteroadhesin agonist antibody can be used to treat neuropathy, and especially peripheral neuropathy. "Peripheral neuropathy" refers to a disorder affecting the peripheral nervous system, most often manifested as one or a combination of motor, sensory, sensorimotor, or autonomic neural dysfunction. The wide variety of morphologies exhibited by peripheral neuropathies can each be attributed uniquely to an equally wide number of causes. For example, peripheral neuropathies can be genetically acquired, can result from a systemic disease, or can be induced by a toxic agent. Examples include but are not limited to distal sensorimotor neuropathy, or autonomic neuropathies such as reduced motility of the gastrointestinal tract or atony of the urinary bladder. Examples of neuropathies associated with systemic disease include post-polio syndrome; examples of hereditary neuropathies include Charcot-Marie-Tooth disease, Refsum's disease, Abetalipoproteinemia, Tangier disease, Krabbe's disease, Metachromatic leukodystrophy, Fabry's disease, and Dejerine-Sottas syndrome; and examples of neuropathies caused by a toxic agent include those caused by treatment with a chemotherapeutic agent.

An anti-ErbB chimeric heteroadhesin agonist antibody of the invention may also be used to treat muscle cells and medical conditions affecting them. For example, the HRG may be used to treat a pathophysiological condition of the musculature in a mammal, such as a skeletal muscle disease (e.g. myopathy or dystrophy), a cardiac muscle disorder (such as atrial cardiac arrhythmias, cardiomyopathy, ischemic damage, congenital disease, or cardiac trauma), or a smooth muscle disorder (for example, arterial sclerosis, vascular lesion, or congenital vascular disease); to treat muscle damage; to decrease atrophy of muscle cells; to increase muscle cell survival, proliferation and/or regeneration in a mammal; to treat hypertension; and/or to treat a muscle cell which has insufficient functional acetylcholine receptors (as in a patient with myasthenia gravis or tachycardia).

An anti-ErbB chimeric heteroadhesin agonist antibody may be used to induce the formation of ion channels in a surface membrane of a cell and/or for enhancing the formation of synaptic junctions in an individual. HRG may be also useful as a memory enhancer and may eliminate the "craving" for nicotine.

The anti-ErbB chimeric heteroadhesin agonist antibody may be used to enhance repair and/or regenerate tissues that produce ErbB receptor(s), especially the ErbB2 receptor. For example, the anti-ErbB chimeric heteroadhesin agonist antibody may be used to treat dermal wounds; gastrointestinal disease; Barrett's esophagus; cystic or non-cystic end stage kidney disease; and inflammatory bowel disease. Similarly, this molecule may be used to promote reepithelialization in the human gastrointestinal, respiratory, reproductive or urinary tract.

It may be desirable to treat the mammal with a HRG antagonist, such as an ErbB-Ig chimeric heteroadhesin, particularly where excessive levels of HRG are present and/or excessive activation of ErbB receptors by HRG is occurring in the mammal. Exemplary conditions or disorders to be treated with a HRG antagonist include benign or malignant tumors (e.g. renal, liver, kidney, bladder, breast, gastric, ovarian, colorectal, prostate, pancreatic, ling, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; inflammatory, angiogenic and immunologic disorders; psoriasis and scar tissue formation. HRG antagonists may also be used to reverse resistance of tumor cells to the immune-response, to inhibit pathological angiogenesis and to stimulate the immune system.

In still further embodiments of the invention, an anti-ErbB chimeric heteroadhesin as a HRG antagonist may be administered to patients suffering from neurologic diseases or disorders characterized by excessive production of HRG and/or excessive ErbB receptor activation by HRG. An anti-ErbB chimeric heteroadhesin antagonist antibody may be used in the prevention of aberrant regeneration of sensory neurons such as may occur post-operatively, or in the selective ablation of sensory neurons, for example, in the treatment of chronic pain syndromes.

There are two major approaches to introducing the nucleic acid (optionally contained in a vector) into the patient's cells; in vivo and ex vivo. For in vivo delivery the nucleic acid is injected directly into the patient, usually at the site where the chimeric heteroadhesin is required. For ex vivo treatment, the patients cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187).

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., J. Biol. Chem. 262:4429–4432 (1987); and Wagner et al., Proc. Natl. Acad. Sci. USA 87:3410–3414 (1990). For review of the currently known gene marking and gene therapy protocols see Anderson et al., Science 256:808–813 (1992). See also WO 93/25673 and the references cited therein.

Therapeutic formulations of a chimeric heteroadhesin or an antibody raised against it are prepared for storage by mixing the heteroadhesin or antibody having the desired degree of purity with optional physiologically acceptable carriers, excipients, or stabilizers (Remington's Pharmaceutical Sciences, 16th Edition, Osol., A., Ed., (1980)), in the form of lyophilized cake or aqueous solutions. Pharmaceutically acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™, or polyethylene glycol (PEG).

A chimeric heteroadhesin or anti-chimeric heteroadhesin antibody to be used for in vivo administration must be sterile. This is readily accomplished by filtration through sterile filtration membranes, prior to or following lyophilization and reconstitution. The formulation ordinarily will be stored in lyophilized form or in solution.

Therapeutic chimeric heteroadhesin or anti-chimeric heteroadhesin antibody compositions generally are placed into a container having a sterile access port, for example, an intravenous solution bag or vial having a stopper pierceable by a hypodermic injection needle.

The route of chimeric heteroadhesin or antibody administration is in accord with known methods, e.g., injection or infusion by intravenous, intraperitoneal, intracerebral, intramuscular, intraocular, intraarterial, or intralesional routes, or by sustained-release systems as noted below. The heteroadhesin or antibody is administered continuously by infusion or by bolus injection.

Suitable examples of sustained-release preparations include semipermeable matrices of solid hydrophobic polymers containing the protein, which matrices are in the form of shaped articles, e.g., films, or microcapsules. Examples of sustained-release matrices include polyesters, hydrogels (e.g., poly(2-hydroxyethyl-methacrylate) as described by Langer et al., J. Biomed. Mater. Res., 15:167–277 (1981) and Langer, Chem. Tech., 12:98–105 (1982) or poly (vinylalcohol)), polylactides (U.S. Pat. No. 3,773,919, EP 58,481), copolymers of L-glutamic acid and gamma ethyl-L-glutamate (Sidman et al., Biopolymers, 22:547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988).

Sustained-release chimeric heteroadhesin or agonist or antagonist anti-heteroadhesin antibody compositions also include liposomally entrapped drug. Liposomes containing HRG are prepared by methods known per se: DE 3,218,121; Epstein et al., Proc. Natl. Acad. Sci. USA 82:3688–3692 (1985); Hwang et al., Proc. Natl. Acad. Sci. USA 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the optimal therapy. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. A chemotherapeutic agent (such as Doxorubicin) is optionally contained within the liposome. See Gabizon et al. J. National Cancer Inst. 81(19):1484 (1989).

The ErbB-Ig chimeric heteroadhesin of the invention may be used to bind and sequester HRG ligand thereby inhibiting ErbB activation in the cell and inhibit a cell proliferation disorder in a patient such as cancer.

A cancer patient to be treated with an ErbB2/3-Ig or ErbB2/4-Ig heregulin antagonist or anti-ErbB-Ig antibody as an antagonist as disclosed herein may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antagonist or may be given simultaneously therewith. For cancer indications, it may be desirable to also administer antibodies against tumor associated antigens or against antiogenic factors, such as antibodies which bind to EGFR, ErbB2, ErbB3, ErbB4, or vascular endothelial factor (VEGF). Alternatively, or in addition, one or more cytokines may be co-administered to the patient.

An effective amount of antagonist to be employed therapeutically will depend, for example, upon the therapeutic objectives, the route of administration, and the condition of the patient. Accordingly, it will be necessary for the therapist to titer the dosage and modify the route of administration as required to obtain the maximum therapeutic effect. A typical dosage might range from about 1 $\mu$g/kg to up to 100 mg/kg of patient body weight, preferably about 10 $\mu$g/kg to 10 mg/kg. Typically, the clinician will administer antagonist until a dosage is reached that achieves the desired effect for treatment of the above mentioned disorders.

3. Non-Therapeutic Methods

An HRG agonist anti-ErbB2/3-Ig antibody or anti-erbB2/4-Ig antibody can be used for growing cells (such as glial and muscle cells) ex vivo. It is desirable to have such populations of cells in cell culture for isolation of cell-specific factors e.g. $P75^{NGFR}$ which is a Schwann cell specific marker. Such factors are useful as diagnostic tools or, in the case of $P75^{NGFR}$, can be used an antigens to generate antibodies for diagnostic use. It is also beneficial to have populations of mammalian cells (e.g. Schwann cells) for use as cellular prostheses for transplantation into mammalian patients (e.g. into areas of damaged spinal cord in an effort to influence regeneration of interrupted central axons, for assisting in the repair of peripheral nerve injuries and as alternatives to multiple autografts).

In accordance with the in vitro methods of the invention, cells comprising an ErbB receptor are provided and placed in a cell culture medium. Suitable tissue culture media are well known to persons skilled in the art and include, but are not limited to, Minimal Essential Medium (MEM), RPMI- 1640, and Dulbecco's Modified Eagle's Medium (DMEM). These tissue culture medias are commercially available from Sigma Chemical Company (St. Louis, Mo.) and GIBCO (Grand Island, N.Y.). The cells are then cultured in the cell culture medium under conditions sufficient for the cells to remain viable and grow in the presence of an effective amount of agonistic antibody. The cells can be cultured in a variety of ways, including culturing in a clot, agar, or liquid culture.

Anti-ErbB-Ig antibodies can be used in the diagnosis of cancers characterized by erbB (e.g. erbB2) overexpression and/or amplification, wherein anti-chimeric heteroadhesin antibodies that cross-react with the ErbB receptor are used. Such diagnostic assay(s) can be used in combination with other diagnostic/prognostic evaluations such as determining lymph node status, primary tumor size, histologic grade, estrogen or progesterone status, tumor DNA content (ploidy), or cell proliferation (S-phrase fraction). See Muss et al., New Eng. J. Med., 330(18):1260–1266 (1994).

The sample as herein defined is obtained, e.g. tissue sample from the primary lesion of a patient. Formalin-fixed, paraffin-embedded blocks are prepared. See Muss et al., supra and Press et al., Cancer Research 54:2771–2777 (1994). Tissue sections (e.g. 4 $\mu$M) are prepared according to known techniques. The extent of anti-ErbB2/3-Ig or anti-erbB2/4-Ig antibody binding to the tissue sections is then quantified.

Generally, the chimeric heteroadhesin or the anti-chimeric heteroadhesin antibody will be labeled either directly or indirectly with a detectable label. Numerous labels are available which can be generally grouped into the following categories:

(a) Radioisotopes, such as $^{35}S$, $^{14}C$, $^{125}I$, $^{3}H$, and $^{131}I$. The $\gamma$-HRG or antibody can be labeled with the radioisotope using the techniques described in Current Protocols in Immunology, Ed. Coligen et al., Wiley Publishers, Vols 1 & 2, for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the chimeric heteroadhesin or antibody using the techniques disclosed in Current Protocols in Immunology, supra, for example. Fluorescence can be quantified using a fluorimeter (Dynatech).

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, $\beta$-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to proteins are described in O'Sullivan et al., Methods for the Preparation of Enzyme-Antibody Conjugates for use in Enzyme Immunoassay, in Methods in Enzym. (ed J. Langone & H. Van Vunakis), Academic press, New York, 73:147–166 (1981).

Examples of enzyme-substrate combinations include, for example: (a) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB)); (b) alkaline phosphatase (AP) with para-Nitrophenyl phosphate as chromogenic substrate; and (c) $\beta$-D-galactosidase ($\beta$-D-Gal) with a chromogenic substrate (e.g. p-nitrophenyl-$\beta$-D-galactosidase) or fluorogenic substrate 4-methylumbelliferyl-$\beta$-D-galactosidase.

Numerous other enzyme-substrate combinations are available to those skilled in the art. For a general review of these, see U.S. Pat. Nos. 4,275,149 and 4,318,980.

Optionally, the label is indirectly conjugated with the chimeric heteroadhesin or anti-CHA antibody. The skilled artisan will be aware of various techniques for achieving this. For example, the CHA or anti-CHA antibody can be conjugated with biotin and any of the three broad categories of labels mentioned above can be conjugated with avidin, or vice versa. Biotin binds selectively to avidin and thus, the label can be conjugated with the CHA or anti-CHA antibody in this indirect manner. See, Current Protocols in Immunology, supra, for a review of techniques involving biotin-avidin conjugation. Alternatively, to achieve indirect conjugation of the label with the CHA or anti-CHA antibody, the CHA or anti-CHA antibody is conjugated with a small hapten (e.g. digoxin) and one of the different types of labels mentioned above is conjugated with an anti-hapten antibody (e.g. anti-digoxin antibody). Thus, indirect conjugation of the label with the CHA or anti-CHA antibody can be achieved.

In another embodiment of the invention, the CHA or anti-CHA antibody need not be labeled, and the presence thereof can be detected using a labeled anti-CHA or anti-antibody antibody (e.g. conjugated with HRPO).

In the preferred embodiment, the HRG or antibody is labeled with an enzymatic label which catalyzes a color change of a substrate (such as tetramethyl benzimidine (TMB), or orthaphenylene diamine (OPD)). Thus, the use of radioactive materials is avoided. A color change of the reagent can be determined spectrophotometrically at a suitable wavelength (e.g. 450 nm for TMB and 490 nm for OPD, with a reference wavelength of 650 nm).

Cells thought capable of expressing a ligand such as HRG are exposed to the labeled ErbB CHA and the intensity of staining of the cell culture medium determined. While in vitro analysis is normally contemplated, in vivo diagnosis using labeled ErbB CHA conjugated to a detectable moiety (e.g. In for imaging) can also be performed. See, e.g., U.S. Pat. No. 4,938,948.

CHAs or anti-CHA antibodies are also useful in a radioimmunoassay, enzyme-linked immunoassay, or radioreceptor assay), in affinity purification techniques (e.g. for HRG, or for an ErbB receptor such as ErbB3 or ErbB4 receptor), and in competitive-type receptor binding assays when labeled with radioiodine, enzymes, fluorophores, spin labels, and the like. Thus, CHAs are useful as immunogens for generating anti-CHA antibodies for diagnostic use.

4. Anti-Chimeric Heteroadhesin Antibodies & Uses Thereof

Techniques for generating antibodies, such as polyclonal and monoclonal antibodies are well known in the art. Polyclonal antibodies generally are raised by immunizing animals with CHA or a fragment thereof (optionally conjugated to a heterologous protein that is immunogenic in the species to be immunized). Monoclonal antibodies directed toward a CHA may be produced using any method which provides for the production of antibody molecules by continuous cell lines in culture. Examples of suitable methods for preparing monoclonal antibodies include the original hybridoma method of Kohler et al., Nature 256:495–497 (1975), and the human B-cell hybridoma method, Kozbor, J., Immunol. 133:3001 (1984); Brodeur et al., Monoclonal Antibody Production Techniques and Applications, pp.51–63 (Marcel Dekker, Inc., New York, 1987); and Boemer et al., J. Immunol. 147:86–95 (1991).

DNA encoding the monoclonal antibodies of the invention is readily isolated and sequenced using conventional procedures (e.g., by using oligonucleotide probes that are capable of binding specifically to genes encoding the heavy and light chains of antibodies). The hybridoma cells of the invention serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (Morrison, et al., Proc. Natl. Acad. Sci. USA 81:6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of an anti-CHA monoclonal antibody herein.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature 321:522–525 (1986); Riechmann et al., Nature 332:323–327 (1988); and Verhoeyen et al., Science 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol, 151:2296 (1993); and Chothia and Lesk, J. Mol. Biol. 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285 (1992); and Presta et al., J. Immnol. 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

According to an alternative method for producing human antibodies, transgenic animals (e.g., mice) are available that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature 362:255–258 (1993); and Bruggermann et al., Year in Immuno. 7:33 (1993).

Alternatively, phage display technology (McCafferty et al., Nature 348:552–553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimicks some of the properties of the B-cell. Phage display can be performed in a variety of formats; for their review see, e.g., Johnson, Kevin S. and Chiswell, David J., Current Opinion in Structural Biology 3:564–571 (1993). Several sources of V-gene segments can be used for phage display. Clackson et al., Nature, 352:624–628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581–597 (1991), or Griffith et al., EMBO J. 12:725–734 (1993).

Bispecific antibodies are antibodies that have binding specificities for at least two different antigens. In the present case, one of the binding specificities is for a CHA (preferably the ECDs of the CHA) the other one is for any other antigen. Bispecific antibodies can be prepared as full length antibodies or antibody fragments (e.g. F(ab')$_2$ bispecific antibodies). Procedures described below are useful for the preparation of bispecific antibodies as well as the preparation of multimerization domains of the CHAs of the invention.

Methods for making bispecific antibodies are known in the art. Traditional production of full length bispecific antibodies is based on the coexpression of two immunoglobulin heavy chain-light chain pairs, where the two chains have different specificities (Millstein et al., Nature 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655–3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175:217–225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing erbB and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al. Proc. Natl. Acad. Sci. USA, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al. J. Immunol. 152:5368 (1994).

Antibodies with more than two valencies are contemplated. For example, trispecific antibodies can be prepared. Tutt et al. J. Immunol. 147:60 (1991).

To manufacture a neutralizing antibody, antibodies are made using the techniques for generating these molecules elaborated above. The preferred neutralizing antibody is specific for the extracellular domain of the CHA and cross-reacts with the extracellular domain of the natural heteromultimeric receptor, but does not cross-react with other receptors. Following production of a panel of antibodies, the antibodies are subjected to a screening process in order to identify those molecules which meet the desired criteria (i.e. which are able to neutralize a biological activity of the natural heteromultimeric receptor either in vitro or in vivo). For example, the ability of the ErbB-Ig CHA to block ErbB activity in any one or more of the assays described above can be evaluated. Those CHAs or anti-CHA antibodies which block the ability of HRG to bind to and/or activate an ErbB receptor and/or the mitogenic activity of HRG on cells can be selected as neutralizing CHAs or CHA antibodies.

The antibodies may be coupled to a cytotoxic agent or enzyme (e.g. a prodrug-activating enzyme) in a similar manner to that described above for a CHA. Furthermore, the antibodies may be labeled as described above, especially where the antibodies are to be used in diagnostic assays.

5. Diagnostic Kits & Articles of Manufacture

Since the invention provides at least two types of diagnostic assay (i.e. for detecting cancer using anti-ErbB-Ig antibody, for example, and for detecting the presence of HRG in a sample using ErbB-Ig, for example) as a matter of convenience, the reagents for these assays can be provided in a kit, i.e., a packaged combination of reagents, for combination with the sample to be tested. The components of the kit will normally be provided in predetermined ratios. Thus, a kit may comprise the CHA or anti-CHA antibody labeled directly or indirectly with a suitable label. Where the detectable label is an enzyme, the kit will include substrates and cofactors required by the enzyme (e.g. a substrate precursor which provides the detectable chromophore or fluorophore). In addition, other additives may be included such as stabilizers, buffers and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the bioassay.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the CHA or an HRG antagonist anti-CHA antibody thereof. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

EXAMPLES

The following examples are offered by way of illustration and not by way of limitation. The examples are provided so as to provide those of ordinary skill in the art with a complete disclosure and description of how to make and use the compounds, compositions, and methods of the invention and are not intended to limit the scope of what the inventors regard as their invention. Efforts have been made to insure accuracy with respect to numbers used (e.g. amounts, temperature, etc. but some experimental errors and deviation should be accounted for. Unless indicated otherwise, parts are parts by weight, temperature is in degrees C, and pressure is at or near atmospheric. The disclosures of all citations in the specification are expressly incorporated herein by reference.

Example 1

Materials and Methods

This example describes the construction, isolation and biochemical characterization of the ErbB2-IgG, ErbB3-IgG, and ErbB4-IgG chimeric amino acid sequences and the resultant chimeric heteromultimers of the present invention.

Reagents

The EGF-like domain of $HRG\beta1_{(177-244)}$ was expressed in *E. coli*, purified and radioiodinated as described previously (Sliwkowski, M. et al. J. Biol. Chem. 269:14661–14665 (1994)). Full-length rHRGβ1, which was expressed in Chinese hamster ovary cells, was used in Western blot analysis. The anti-ErbB2 monoclonal antibodies 2C4 and 4D5 have been described elsewhere (Fendly et al. Cancer Research 50:1550–1558 (1990)).

ErbB2-, ErbB3- and ErbB4-immunoadhesins

A unique Mlu I site was engineered into a plasmid expressing human IgG heavy chain (pDR, a gift from J. Ridgeway and P. Carter, Genentech, Inc.) at the region encoding the hinge domain of the immunoglobulin Mlu I sites were also engineered into a set of ErbB expression plasmids at the region encoding the ECD/TM junctions of these receptors. All mutageneses were done using the Kunkel method (Kunkel, T., Proc. Natl. Acad. Sci. U.S.A 82:488 (1985)). The Mlu I sites were utilized to make the appropriate ErbB-IgG fusion constructs. The fusion junctions of the various ErbB-IgG chimeras were: for ErbB2, $E^{646}_{ErbB2}$-(TR)-DKTH$^{224}_{VH}$; for ErbB3, $L^{636}_{ErbB3}$-(TR)-DKTH$^{224}_{VH}$; for ErbB4, $G^{640}_{ErbB4}$-(TR)-DKTH$^{224}_{VH}$, where the amino acid numbering of the ErbB polypeptides is described in Plowman et al. (Plowman, G. D. et al., (1993a) PNAS USA 90:1746–1750). The conserved TR sequence is derived from the Mlu I site. The sequence of the Fc region used in the preparation of the fusion constructs is found in Ellison, J. W. et al. (Ellison, J. W. et al. (1982) NAR 10:4071–4079). The final expression constructs were in a pRK-type plasmid backbone wherein eukaryotic expression is driven by a CMV promoter (Gorman et al., DNA Prot. Eng. Tech. 2:3–10 (1990)).

To obtain protein for in vitro experiments, adherent HEK-293 cells (ATCC No. CRL-1573) were transfected with the appropriate expression plasmids using standard calcium phosphate methods (Gorman et al., supra and Huang et al., Nucleic Acids Res. 18:937–947 (1990)). Serum-containing media was replaced with serum-free media 15 hours post-transfection and the transfected cells incubated for 5–7 days. The resulting conditioned media was harvested and passed through Protein A columns (1 mL Pharmacia HiTrap™). Purified IgG fusions were eluted with 0.1 M citric acid (pH 4.2) into tubes containing 1 M Tris pH 9.0. The eluted proteins were subsequently dialyzed against PBS and concentrated using Centri-prep-30 filters (Amicon). Glycerol was added to a final concentration of 25% and the material stored at –20° C. Concentrations of material were determined via a Fc-ELISA.

$^{125}$I-HRG Binding Assay

Binding assays were performed in Nunc breakapart immuno-module plates. Plate wells were coated at 4° C. overnight with 100 µl of 5 µg/ml goat-anti-human antibody (Boehringer Mannheim) in 50 mM carbonate buffer (pH 9.6). Plates were rinsed twice with 200 µl wash buffer (PBS/0.05% Tween-20™) followed by a brief incubation with 100 µl 1% BSA/PBS for 30 min at room temperature. Buffer was removed and each well was incubated with 100 µl IgG fusion protein in 1% BSA/PBS under vigorous side-to-side rotation for 1 hour. Plates were rinsed three times with wash buffer and competitive binding was carried out by adding various amounts of cold competitor γ-HRG and $^{125}$I-HRGβ1 and incubating at room temperature for 2–3 hours with vigorous side-to-side rotation. Wells were quickly rinsed three times with wash buffer, drained and individual wells were counted using a 100 Series Iso Data γ-counter. Scatchard analysis was performed using a modified Ligand program (Munson, P. and Robard, D. (1980) Analytical Biochemistry 107:220–239).

$^3$H-Thymidine Incorporation Assay

Tritiatedthymidine incorporation assays were performed in a 96-well format. MCF7-7 cells were plated at 10,000 cells/well in 50:50 F12/DMEM (high glucose) 0.1% fetal calf serum (100 mL). Cells were allowed to settle for 3 hours, after which ErbB-IgG fusion proteins and/or heregulin were added to the wells (final volume of 200 mL) and the plates incubated for 15 hours in a 37° C. tissue culture incubator. Tritiated thymidine was added to the wells (20 mL of 1/20 diluted tritiated thymidine stock: Amersham TRA 120 B363, 1 mCi/mL) and the plates incubated a further 3 hours. Tritiated material was then harvested onto GF/C unifilters (96 well format) using a Packard Filtermate 196 harvester. Filters were counted using a Packard Topcount apparatus.

Example 2

ErbB3-IgG and ErbB4-IgG Proteins Bind HRG

Figure 2:
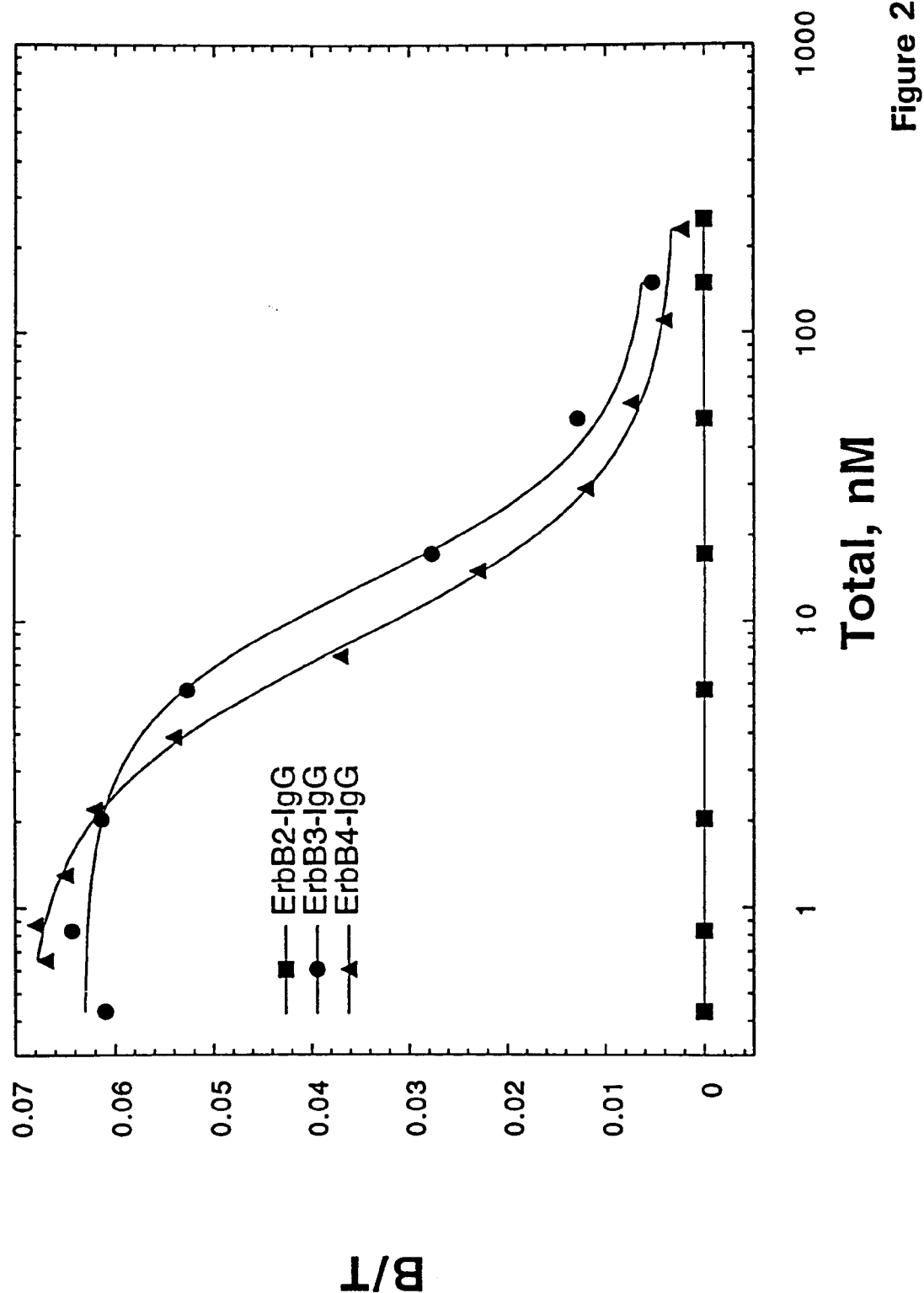
FIG. 2 is a graphical plot showing the binding analysis of the chimeric immunoadhesin. The homodimeric ErbB3-IgG and ErbB4-IgG were capable of specifically binding $^{125}$I-HRG, whereas no discernible binding was detected with the ErbB2-IgG construct.

As described above, a series of plasmid constructs were prepared that permitted the eukaryotic expression of the extracellular domains (ECDs) of ErbB receptors fused to the constant domains of human IgG. As depicted in FIG. 1, these receptor-IgG constructs exist in solution as disulfide-linked dimers. Homodimeric IgG receptors for ErbB2, ErbB3 and ErbB4 were individually expressed in HEK-293 cells and the resulting secreted receptor fusion proteins were purified by affinity chromatography on protein A. Chen et al. (Chen, X. et al., (1996) J. Biol. Chem. 271:7620–7629) reported a similar construction of the homodimeric ErbB3- and ErbB4-immunoadhesins, which were used as immunogens for the generation of receptor-specific monoclonal antibodies. Binding analysis of the chimeric immunoadhesin proteins was performed using a microtiter plate format (see Example 1). As shown in FIG. 2, the homodimeric ErbB3-IgG and ErbB4-IgG were capable of specifically binding $^{125}$I-HRG, whereas no discernible binding was detected with the ErbB2-IgG construct. Scatchard analysis of HRG binding to ErbB3-IgG displayed a single affinity binding site with a $K_d$ of 9.3±2.9 nM. Binding constants for detergent-solubilized ErbB3 expressed in insect cells (Carraway et al., 1994), ErbB3 expressed in COS7 cells (Sliwkowski et al., (1994) supra) and ErbB3 expressed in K562 cells ranged between 0.8 to 1.9 nM. Homodimeric ErbB3-IgG has a higher affinity constant for HRG than the value of 26 nM recently reported by Horan et al. (Horan et al., (1995) J. Biol. Chem. 270:24604–24608) in an analysis that used a monovalent soluble ECD of ErbB3. These data suggest that the optimal conformation of the HRG binding site on ErbB3 may be stabilized by a lipid bilayer. A greater loss in binding affinity relative to the intact receptor, has also been reported for soluble versions of the EGF receptor (Brown, P. M. et al., (1994) Eur. J. Biochem. 225:223–233; and Zhou, M. et al., (1993) Biochemistry 32:8193–8198). The affinity constant measured for the ErbB4-IgG was 5.0±0.8 nM. This value is in close agreement with that reported by Tzahar et al. of 1.5 nM for fill-length ErbB4 expressed in COS7 cells (Tzahar, E. et al., (1994) J. Biol. Chem. 269:25226–25233).

Although neuregulins are a family of proteins arising from alternative RNA splicing, receptor binding is mediated by the EGF-like motif present in all active isoforms. Chimeric homodimer immunoadhesins containing the ECDs of ErbB3 or ErbB4 bound multiple forms of the neuregulin family provided that the EGF-like domain of these proteins were present. The heregulin variants that bound these homodimers included rHRGβ1$_{1-244}$, rHRGβ$_{144-244}$, thioredoxine-HRGβ$_{144-244}$, and thioredoxine-γHRG, rHRGα$_{1-239}$.

Example 3

Heterodimeric ErbB-IgG Fusion Proteins Form a High Affinity HRG Binding Site when ErbB2 is Present with ErbB3 or ErbB4

Figure 3:
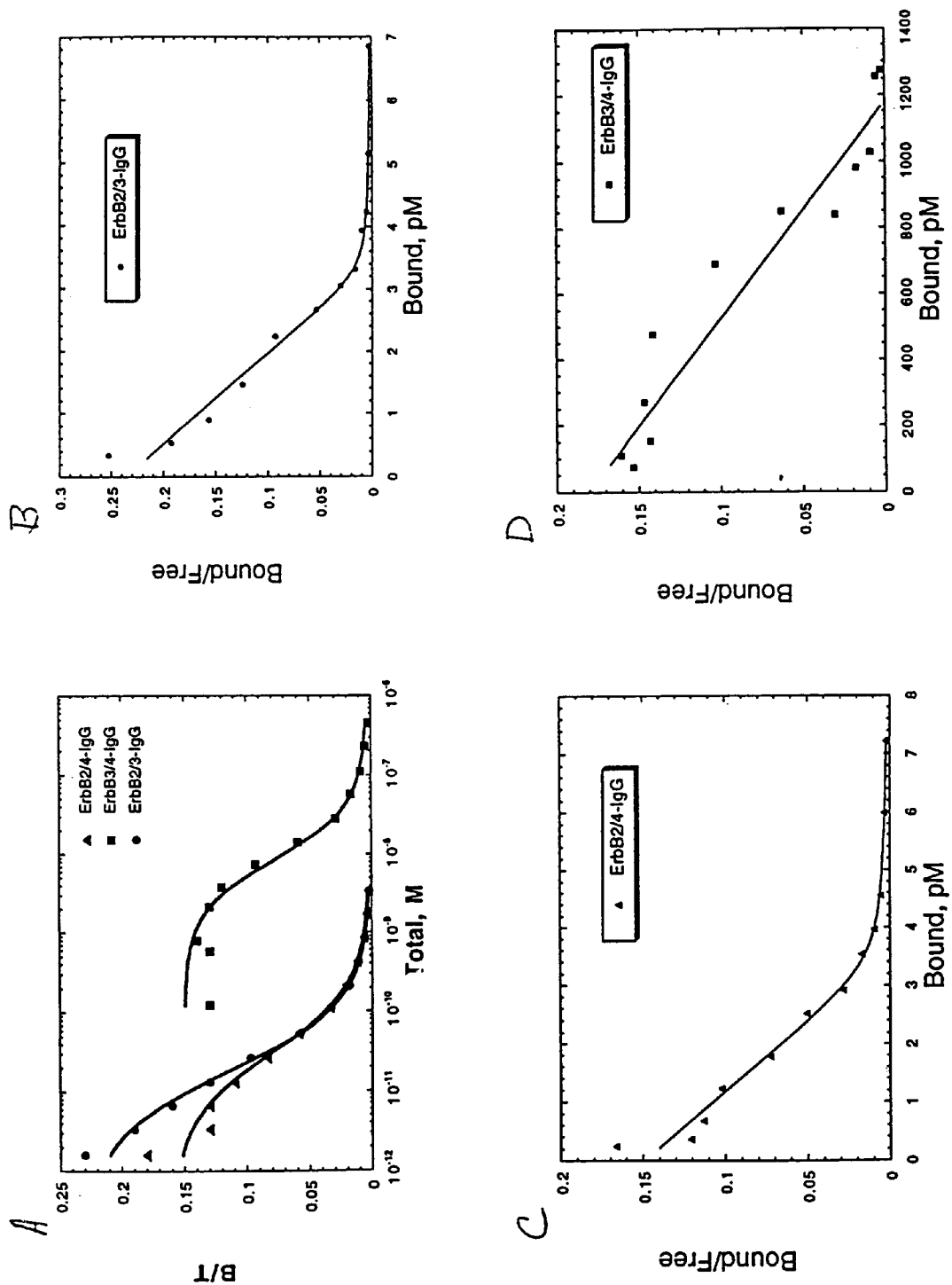
FIGS. 3A–3D are graphical results of $^{125}$I-heregulin binding studies for each of the chimeric heteroadhesins ErbB2/3-IgG, ErbB2/4-IgG and ErbB3/4-IgG.

Heterodimeric versions of the receptor-IgG constructs were generated by co-transfecting two expression plasmids encoding different receptors into the same cell (see Example 1). The resulting secreted forms of the receptor-IgGs are mixtures of two types of homodimers and the expected heterodimer. Three different cotransfections were performed to generate the following ErbB mixtures: ErbB2/3-IgG, ErbB2/4-IgG and ErbB3/4-IgG. Binding affinities for each of the mixtures were then determined. As shown in FIG. 3A, a high affinity HRG binding site could be detected with the ErbB2-containing heterodimers but not the ErbB3/4-IgG. Scatchard plots of these data were curvilinear for the ErbB2-containing heterodimer mixtures (FIGS. 3B and 3C) suggesting the presence of two-distinct types of binding sites (Munson, P. and Robard, D. (1980) Analytical Biochem. 107:220–239). A $K_d$ of 0.013 nM was measured for the high affinity binding site, whereas the low affinity binding site had a $K_d$ of 12 nM. The high affinity binding constant is in agreement with the values measured when ErbB3 is expressed in cells containing high levels of ErbB2 (Carraway et al., (1994) supra) or when high affinity HRG binding sites are determined from a 2-site fit of binding data in high ErbB3 backgrounds (Sliwkowski et al., (1994) supra). ErbB2/4-IgG (FIG. 3C) also exhibited a similar affinity shift when compared to the ErbB4-IgG homodimer. The measured affinity constant for the ErbB2/4-IgG was 0.017 nM. Again using a 2-site fit, a low affinity binding site $K_d$ of 5 nM was measured. This value is in close agreement with the $K_d$ measured for the ErbB4-IgG homodimer. In contrast, the ErbB3/ErbB4-IgG protein (FIG. 3D) did not display a high affinity site, but instead a $K_d$ of 6 nM was measured, which was comparable to that seen for the ErbB3-IgG and ErbB4-IgG homodimers. The formation of a high affinity ligand binding site correlated with the co-expression of the ErbB2 ECD with an ECD of another member of the ErbB family, suggesting ErbB2 was required for the formation of a high affinity site. A summary of binding constants for the ErbB-IgG fusion proteins is shown in Table I. The high affinity binding site that was formed for the heterodimeric ErbB2/3-IgG or ErbB2/4-IgG protein was 300–700 fold higher than for the corresponding homodimeric species.

TABLE I

Binding Constants For ErbB Homodimer and Heterodimer Immunoadhesins

| ErbB-IgG Construct | Kd (nM) |
|---|---|
| ErbB2 | NB* |
| ErbB3 | 9.24 ± 2.94 |
| ErbB4 | 4.98 ± 0.80 |
| ErbB2/3 | 0.013 ± 0.004 |
| ErbB2/4 | 0.017 ± 0.009 |
| ErbB3/4 | 5.98 ± 0.70 |

*NB indicates no measurable binding

Figure 4:
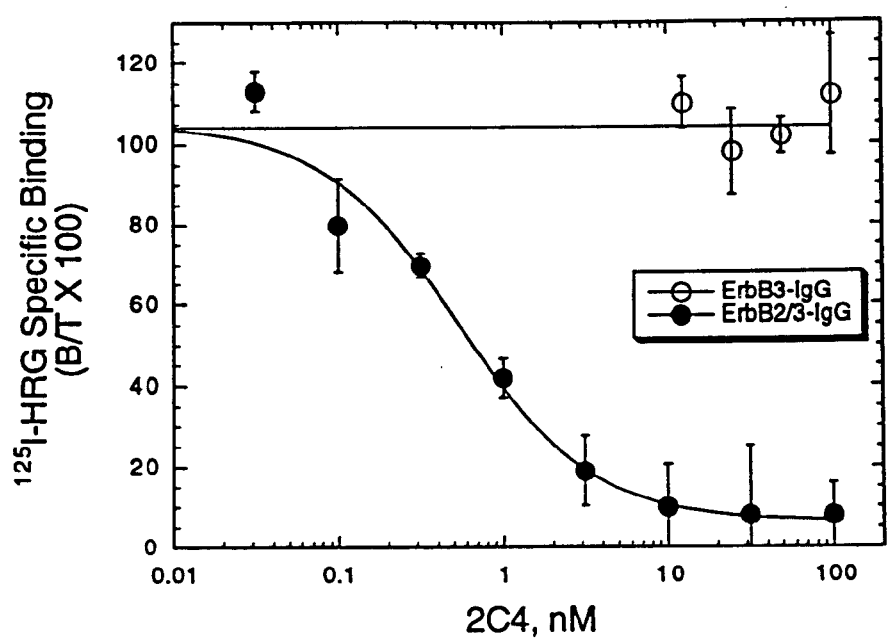
FIGS. 4A and 4B are graphical results of anti-ErbB2 monoclonal antibody (2C4) binding studies in which the binding activity of chimeric ErbB homodimers is compared to that of chimeric ErbB heterodimers in the presence of 2C4.
Figure 4:
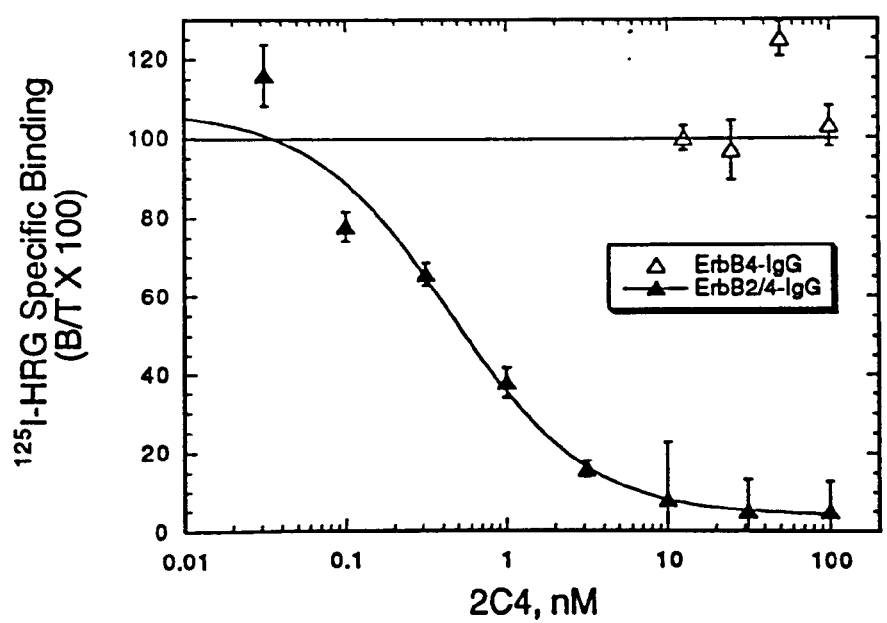

To further test the hypothesis that ErbB2 was contributing to the formation of the high affinity binding site, the effect of an anti-ErbB2 ECD antibody to inhibit high affinity binding to the ErbB immunoadhesins was examined. Binding reactions were conducted in the presence of an antibody, 2C4, which is specific for the ErbB2 ECD (Lewis, G. D. et al. (1996) Cancer Res. 56:1457–1465; Sliwkowski et al., (1994) supra). As shown in FIG. 4A, the addition of the 2C4 monoclonal antibody had a marked inhibitory effect on HRG binding for the ErbB2/ErbB3-IgG heterodimer but not for the corresponding ErbB3-IgG homodimer. Similarly, the anti-ErbB2 monoclonal antibody also effected HRG binding to the ErbB2/ErbB4-IgG heterodimer (FIG. 4B) but not to the corresponding ErbB4-IgG homodimer. These data indicate that the physical interaction of the ECD of ErbB2 with the ECD of either ErbB3 or ErbB4 results in the formation of a high affinity growth factor binding site in this soluble receptor system.

Example 4
ErbB-IgG Fusion Proteins Inhibit the Biological Effects of HRG

Figure 5:
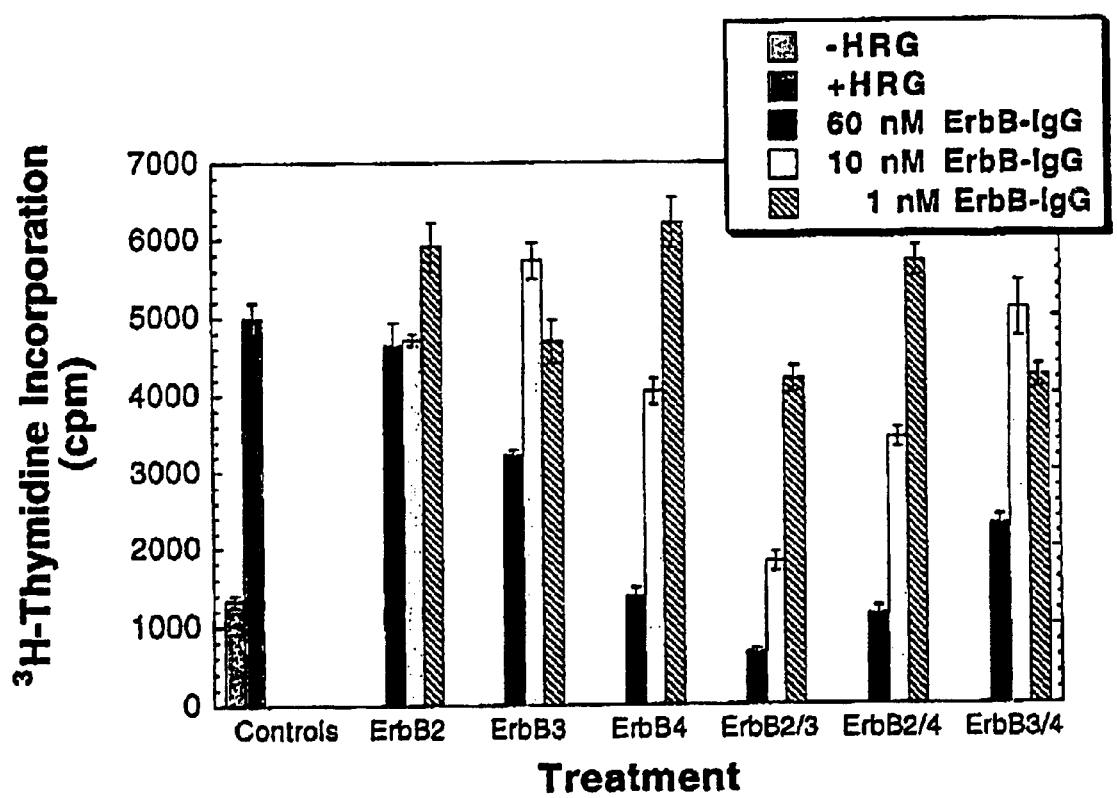
FIG. 5 is a bar graph indicating the ability of the ErbB-IgG proteins to inhibit HRG-dependent thymidine incorporation in the breast carcinoma cell line, MCF7. Varying concentrations of the different ErbB-IgG proteins were incubated with 1 nM rHRG and then added to serum-starved monolayer cultures of MCF7 cells. Cells were labeled with $^3$H-thymidine to measure DNA synthesis. Receptor fusions capable of HRG binding inhibited the HRG-mediated mitogenic response in a dose related manner. The heterodimeric IgGs, ErbB3/2-IgG and ErbB4/2-IgG, were more potent than their corresponding homodimeric fusion proteins.

Upon HRG treatment, a number of different cell types are known to undergo proliferative responses. The ability of the ErbB-IgG proteins to inhibit HRG-dependent thymidine incorporation was tested in the breast carcinoma cell line, MCF7 (Lewis et al., (1996) supra). Varying concentrations of the different ErbB-IgG proteins were incubated with 1 nM rHRG and then added to serum-starved monolayer cultures of MCF7 cells (see Example 1). Following a 24 h incubation, cells were then labeled with ³H-thymidine to measure DNA synthesis. As shown in FIG. 5, all receptor fusions capable of HRG binding, inhibited the HRG-mediated mitogenic response in a dose related manner. The heterodimeric IgGs, ErbB3/2-IgG and ErbB4/2-IgG, were more potent than their corresponding homodimeric fusion proteins.

DISCUSSION
The Extracellular Domain of ErbB2 Modulates the Binding of HRG to ErbB3 and ErbB4

Immunoadhesins offer a number of advantages for in vitro analysis (see Chamow, S. M. and Ashkenazi, A. (1996) Trends in Biotechnology 14:52–60, for review). It is the dimerization capacity of the IgG fusions which appears to mimic the putative in vivo heterodimerization of the ErbB family of receptor resulting in the generation of the high affinity heregulin binding site. HRG binding analysis demonstrated that heterodimeric mixtures that included ErbB2, i.e., ErbB2/ErbB3-IgG and ErbB2/ErbB4-IgG, produced a heregulin binding site with greater than 300 fold higher affinity than that seen for ErbB3-IgG or ErbB4-IgG homodimers or the ErbB3/ErbB4-IgG heterodimer. The low affinity HRG binding site present in the ErbB3/ErbB4-IgG heterodimer suggests that the creation of a high affinity heregulin binding site cannot be made by the combination of any two different ErbB-IgGs, but rather is specific to ErbB2-IgG containing mixtures. Further evidence for the requirement of ErbB2 to generate this high affinity binding site was determined with monoclonal antibodies directed against ErbB2 (Lewis et al., (1996) supra; Sliwkowski et al., (1994) supra). When binding studies were conducted with ErbB2-containing heterodimers in the presence of these antibodies a significant decrease in HRG binding affinity was observed.

The formation of the HRG-ErbB3-ErbB2 complex occurs sequentially in cell lines that express normal levels of these receptors. Specifically, HRG binds to ErbB3 and ErbB2 is then recruited to this HRG occupied receptor. The formation of the complex results in a decrease in the dissociation rate of the ligand, generating a high affinity binding site (Karunagaran, D. et al. (1996) EMBO J. 15:254–264). Now it is reported that formation of the high affinity complex also occurred in a soluble receptor system in the absence of transmembrane and intracellular domains, provided that a dimerization motif was present. In contrast, Horan et al. (Horan, T. et al. (1995) J. Biol. Chem. 270:24604–24608) reported no apparent increase in HRG binding to ErbB3-ECD upon the addition of ErbB2-ECD. In agreement with those findings, a similar result is obtained if homodimeric ErbB-IgGs produced from singly transfected cells were mixed and tested for heregulin binding. The resultant mixtures of ErbB2-IgG homodimers mixed with homodimers of ErbB3-IgG or ErbB4-IgG did not exhibit any greater ligand affinity than ErbB3-IgG or ErbB4-IgG alone. The dimerization motif supplied by the Fc component is thus an important feature in the formation of a high affinity ligand binding site. Moreover, the flexibility of the hinge region may also assist in facilitating these receptor-ligand interactions. Without being limited to any one theory, with intact receptors embedded in a cell membrane, other motifs, such as the transmembrane domains or the intracellular domain, may also contribute to the stabilization of ErbB2 containing hetero-oligomeric complexes.

The Role of ErbB2 in an Oligomeric Heregulin-receptor Signaling Complex

Figure 6:
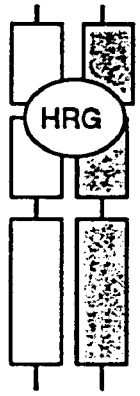
FIG. 6 is a diagram depicting possible models for the interaction of ErbB2 with ErbB3 or ErbB4, a "contact" model (left) and a "conformational" model (right).
Figure 6:
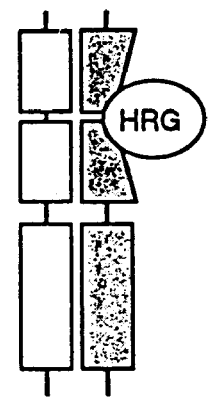

Ligand-induced receptor oligomerization is a common paradigm for single-transmembrane pass receptors (Ullrich, A. and Schlessinger, J. (1990) Cell 61:203–212; and Wells, J. A. (1994) Curr. Opin. Cell Biol. 6:163–173). Based on the discovery herein of a soluble chimeric heterodimer composed of either ErbB3 or ErbB4 with ErbB2, it is concluded that such a chimeric heterodimer is sufficient for the formation of a high affinity binding state. Two possible models that are consistent with these data (FIG. 6) are proposed. The 'contact' model is analogous to that developed for growth hormone and its receptor (Wells, J. A. (1996) PNAS USA 93:1–6 ), except that site 1 resides on ErbB3 or ErbB4 and site 2 is contributed by ErbB2. This model predicts that the affinity for HRG binding to site 1 would be similar to that measured for the ErbB3 or ErbB4 homodimers. ErbB2 is then recruited to the ErbB3-HRG or ErbB4-HRG complex, and contacts the ErbB3 (or ErbB4)-bound HRG. The formation of the ErbB3-HRG-ErbB2 complex decreases the dissociation of HRG and generates the higher affinity binding state. Alternatively, the 'conformation' model postulates that ErbB2 modulates the interaction of HRG with ErbB3 or ErbB4, but contact between HRG and ErbB2 does not occur. In this model the interaction of ErbB2 with ErbB3 or ErbB4 alters the conformation of these receptors and creates a high affinity binding state.

Using chemical cross-linking techniques with radiolabeled HRG on cells expressing ErbB3 and ErbB2 (Holmes, W. E. et al., (1992) Science 256:1205–1210; Sliwkowski et al., (1994) supra), cross-linked complexes corresponding to proteins with molecular sizes of approximately 190 kDa and greater than 500 kDa were observed. These results suggest that the oligomeric structure of the receptor complex may include multiple copies of ErbB3 and ErbB2. Moreover, since ErbB3 is devoid of intrinsic tyrosine kinase activity (Guy et al., (1994) supra), this hypothesis offers an explanation for the ligand-dependent increase in tyrosine phosphorylation that is observed for both ErbB2 and ErbB3. For example, a complex that contains two copies of ErbB3 and two copies of ErbB2 would allow for phosphorylation of ErbB3, and the transphosphorylation of the secondary ErbB2 receptors as well. TNF receptor homodimer immunoadhesins (Ashkenazi, A. et al., (1991) PNAS USA 88:10535–10539) appear to mimic the TNF receptor system in which the cell surface TNF receptor is a trimer (Banner, D. W. et al., (1993) Cell 73–431–445).

Biological Implications of ErbB2 Modulation of ErbB3 and ErbB4

Since ErbB2 was discovered, it has been assumed that a ligand must exist which solely interacts with and activates ErbB2. Although numerous candidate proteins have been put forth as putative ligands for ErbB2 (reviewed in Hynes, N. E. and Stern, D. F. (1994) Biochem. Biophys. Acta 1198:165–184), no protein has been characterized at the molecular level which fulfills this criterion. Other studies have suggested that ErbB2 appears to play a multi-faceted role in both EGF and heregulin receptor complexes (Earp et al., (1995) supra; Karunagaran et al., (1996) supra. The functions of ErbB2 in these complexes include altering the affinity of the ligand binding domain, contributing a very potent tyrosine kinase component and providing tyrosine residues which upon phosphorylation provide activation and amplification of various signal transduction pathways. Heregulin activation of ErbB2 is physiologically relevant at neural-muscular junctions (Altiok, N. et al., (1995) EMBO J. 14:4258–4266; Chu, G. C. et al., (1995) Neuron 14:329–339; and Jo, S. A. et al., (1995) Nature 373:158–161) and at neural-Schwann cell junctions (Dong, Z. et al. (1995) Neuron 15:585–596; Marchionni, M. A. et al. (1993) Nature 362:312–318; and Morrissey, T. K. et al. (1995) PNAS USA 92:1431–1435). In cell culture experiments using human tumor cell lines, several reports have shown that ablating the interaction of ErbB2 with either ErbB3 or ErbB4 diminishes downstream signaling as well as subsequent biological responses such as growth (Karunagaran et al., (1996) supra; Lewis et al., (1996) supra; Pinkas-Kramarski, R. et al., (1996) EMBO J. 15:2452–2467). The concept of ErbB2 as a permanent 'orphan' receptor (Lonardo et al., 1990) is further supported by recent reports on the phenotypes of the ErbB2 and neuregulin knockouts. In both cases, mice that are homozygous for either mutation were embryonic lethal near E10.5 (Lee, K.-F. et al. (1995) Nature 378:394–398; and Meyer, D. and Birchmeier, C. (1995) Nature 378:386–390). In each case, the embryos died of a similar cardiac phenotype, the lack of ventricular trabeculation. Both embryos also had strikingly similar malformations of the hindbrain. These observations further suggest that ErbB2 is critical to transduce HRG signaling. Under normal biological circumstances, ErbB2's sole function appears to be to mediate HRG and EGF ligand responses as a common member of these receptor complexes.

Although the invention has been described with reference to the presently preferred embodiment, it should be understood that various modifications can be made without departing from the spirit of the invention. Accordingly, the invention is limited only by the following claims.

What is claimed is:

1. An isolated recombinant chimeric heteromultimer adhesin consisting of:
    a first amino acid sequence comprising an extracellular domain of the ErbB2 receptor monomer, or fragment thereof, and a first heterologous multimerization domain;
    an additional amino acid sequence comprising an extracellular domain of the ErbB4 receptor monomer or ligand binding fragment thereof and a second heterologous multimerization domain;
    wherein the multimerization domain of the first amino acid sequence and additional amino acid sequence each comprises an immunoglobulin constant region or fragment thereof; and
    wherein the first amino acid sequence and the additional amino acid sequence are brought together via interaction of the multimerization domain of the first amino acid sequence and the multimerization domain of the additional amino acid sequence to form a ligand binding domain of the chimeric heteromultimer adhesin having a higher affinity for a ligand relative to a monomer of either receptor or a homomultimer of either receptor; and
    wherein the chimeric heteromultimer adhesin is soluble in an aqueous solution.

2. The isolated chimeric heteromultimer adhesin of claim 1, wherein the ligand is a neuregulin.

3. An isolated nucleic acid sequence encoding an amino acid sequence of the chimeric heteromultimer adhesin of claim 1.

4. The isolated nucleic acid of claim 3 further comprising a promoter operably linked to the nucleic acid molecule.

5. A vector comprising the isolated nucleic acid of claim 4.

6. A host cell comprising the nucleic acid of claim 3.

7. A composition comprising the chimeric heteromultimer adhesin of claim 1 and a pharmaceutically acceptable carrier.

8. A composition consisting of a first nucleic acid encoding a first amino acid sequence comprising an extracellular domain of the ErbB2 receptor monomer or fragment thereof and a first heterologous multimerization domain; and a second isolated nucleic acid sequence encoding an additional amino acid sequence comprising an extracellular domain of the ErbB4 receptor monomer or ligand binding fragment thereof and a second heterologous multimerization domain, wherein the first and additional amino acid sequence form a chimeric heteromultimeric adhesin having a higher affinity for a ligand relative to a monomer of either receptor or a homomultimer of either receptor.

9. A host cell comprising the composition of claim 8.

* * * * *

UNITED STATES PATENT AND TRADEMARK OFFICE
CERTIFICATE OF CORRECTION

PATENT NO.    : 6,696,290 B2
DATED         : February 24, 2002
INVENTOR(S)   : Fitzpatrick et al.

It is certified that error appears in the above-identified patent and that said Letters Patent is hereby corrected as shown below:

Title page,
Item [56], References Cited, OTHER PUBLICATIONS, "Collesi et al." reference, "Constitutuive" should read -- Constitutive --

Column 5,
Line 51, "amine" should read -- amino --

Column 15,
Line 66, "referes" should read -- refers --

Column 24,
Line 55, "Affect" should read -- affect --

Column 25,
Line 1, "motoneuron" should read -- motorneuron --

Column 26,
Line 29, "patients" should read -- patient's --

Column 37,
Line 38, "Tritiatedthymidine" should read -- Tritiated thymidine --

Column 38,
Line 24, "fill-length" should read -- full-length --

Signed and Sealed this

Thirteenth Day of July, 2004

JON W. DUDAS
*Acting Director of the United States Patent and Trademark Office*